(12) United States Patent
Whitsett et al.

(10) Patent No.: US 11,672,806 B2
(45) Date of Patent: *Jun. 13, 2023

(54) METHODS AND COMPOSITIONS FOR TREATING MESOTHELIOMA AND SMALL LUNG CANCER THAT EXPRESS MIDKINE

(71) Applicant: Children's Hospital Medical Center, Cincinnati, OH (US)

(72) Inventors: Jeffrey A. Whitsett, Cincinnati, OH (US); Yutaka Maeda, Cincinnati, OH (US); Takuya Fukazawa, Okayama (JP)

(73) Assignee: CINCINNATI CHILDREN'S HOSPITAL MEDICAL CENTER, Cincinnati, OH (US)

( * ) Notice: Subject to any disclaimer, the term of this patent is extended or adjusted under 35 U.S.C. 154(b) by 212 days.

This patent is subject to a terminal disclaimer.

(21) Appl. No.: 17/308,179

(22) Filed: May 5, 2021

(65) Prior Publication Data

US 2021/0315903 A1     Oct. 14, 2021

Related U.S. Application Data

(60) Continuation of application No. 16/857,285, filed on Apr. 24, 2020, now Pat. No. 11,026,950, which is a division of application No. 16/312,478, filed as application No. PCT/US2017/044335 on Jul. 28, 2017, now Pat. No. 10,668,078.

(Continued)

(51) Int. Cl.
| | |
|---|---|
| *A61K 31/5377* | (2006.01) |
| *A61K 31/429* | (2006.01) |
| *A61P 35/00* | (2006.01) |
| *A61K 31/4427* | (2006.01) |

(Continued)

(52) U.S. Cl.
CPC ........ *A61K 31/5377* (2013.01); *A61K 31/429* (2013.01); *A61K 31/4375* (2013.01); *A61K 31/444* (2013.01); *A61K 31/4427* (2013.01); *A61P 35/00* (2018.01)

(58) Field of Classification Search
CPC .............. A61K 31/429; A61K 31/4375; A61K 31/4427; A61K 31/444; A61K 31/5377; A61P 35/00
See application file for complete search history.

(56) References Cited

U.S. PATENT DOCUMENTS

| | | | |
|---|---|---|---|
| 9,168,257 B2 | 10/2015 | Starczynowski et al. | |
| 9,664,682 B2 | 5/2017 | Baron et al. | |
| (Continued) | | | |

FOREIGN PATENT DOCUMENTS

| | | |
|---|---|---|
| WO | WO 2010/094009 A2 | 8/2010 |
| WO | WO 2010/127191 A1 | 11/2010 |
| | (Continued) | |

OTHER PUBLICATIONS

Ayoola A, et al., Primary and Acquired Resistance to Epidermal Growth Factor Receptor Tyrosine Kinase Inhibitors in Non-Small Cell Lung Cancer: An Update, Cancer Invest. 2012; 30:433-46, 14 pgs.

(Continued)

*Primary Examiner* — Savitha M Rao
(74) *Attorney, Agent, or Firm* — Nicole M. Tepe

(57) ABSTRACT

Embodiments provided herein relate to methods and compositions for treating mesothelioma and/or a small cell lung cancer that express midkine.

9 Claims, 14 Drawing Sheets

Related U.S. Application Data

(60) Provisional application No. 62/367,832, filed on Jul. 28, 2016.

(51) Int. Cl.
*A61K 31/4375* (2006.01)
*A61K 31/444* (2006.01)

(56) References Cited

U.S. PATENT DOCUMENTS

| | | |
|---|---|---|
| 9,855,273 B2 | 1/2018 | Starczynowski et al. |
| 10,391,084 B2 | 8/2019 | Whitsett et al. |
| 10,668,078 B2 | 6/2020 | Whitsett et al. |
| 11,026,950 B2 | 6/2021 | Whitsett et al. |
| 2010/0278921 A1 | 11/2010 | Fischer et al. |
| 2013/0085157 A1 | 4/2013 | Smith et al. |
| 2016/0113909 A1 | 4/2016 | Whitsett et al. |

FOREIGN PATENT DOCUMENTS

| | | |
|---|---|---|
| WO | WO 2014/081633 A1 | 5/2014 |
| WO | WO 2014/190163 A2 | 11/2014 |
| WO | WO 2014/205132 A2 | 12/2014 |

OTHER PUBLICATIONS

Choi YL, et al., EML-4ALK Mutations in Lung Cancer that Confer Resistance to ALK Inhibitors, N. Engl. J. Med. 2010; 363:1734-9, 6 pgs.
Easton, et al., mTOR and cancer therapy, Oncogene, 2006, 25:6436-6446, 11 pgs.
Ezquerra L, et al., Midkine, a newly discovered regulator of the renin-angiotensin pathway in mouse aorta: Significance of the pleiotrophin/midkine developmental gene family in angiotensin II signaling, Biochem. Biophys. Res. Commun. 2005; 333:636-43, 8 pgs.
Ferlay J, et al., Estimates of worldwide burden of cancer in 2008: GLOBOCAN 2008, Int. J. Cancer 2010; 127:2893-917, 25 pgs.
Fukazawa, T., et al., "Abstract 2085: Development of a novel targeted therapy for malignant mesothelioma carcinoma by a midkine inhibitor," Cancer Research, Jul. 2017, 4 pgs.
Gandhi, et al., "Phase I Study of Navitoclax (ABT-263), a Novel Bcl-2 Family Inhibitor, in Patients With Small-Cell Lung Cancer and Other Solid Tumors," Journal of Clinical Oncology, Mar. 2011, 29(7):909-916, 8 pgs.
Gennaro, A.R., Ed., *Remington: The Science and Practice of Pharmacy*, 19th Ed., Jun. 1995, Mack Publishing Company, Easton, PA. Table of Contents only, 6 pgs.
Gennaro, A.R., Ed., *Remington: The Science and Practice of Pharmacy*, 20th Ed., Dec. 2000, Lippincott Williams & Wilkins, Baltimore, MD. Table of Contents only, 5 pgs.
Gennaro, A.R., Ed., *Remington's Pharmaceutical Sciences*, 18th Ed., 1990, Mack Publishing Company, Easton, PA. Table of Contents only, 8 pgs.
Hao, et al., Inhibition of the Growth Factor MDK/Midkine by a Novel Small Molecule Compound to Treat Non-Small Cell Lung Cancer. PLOS ONE 8(8):e71093 (2013), 8 pgs.
Heist RS, et al., Genetic Changes in Squamous Cell Lung Cancer, A Review, J. Thorac. Oncol. 2012; 7:924-33, 10 pgs.
Horiba M, et al., Neointima formation in a restenosis model is suppressed in midkine-deficient mice, J. Clin. Invest. 2000; 105:489-95, 7 pgs.
Huang et al., Tycosyl-DNA Phosdiesterase 1 (Tdp1) Inhibitors, Expert Opin Ther Pat 2011, 21 (9), 1285-1292, 10 pgs.
Ikematsu S, et al., Serum midkine levels are increased in patients with various types of carcinomas, Br. J. Cancer 2000; 83:701-6, 6 pgs.
Jemal A, et al., Global Cancer Statistics, CA—Cancer J. Clin. 2011; 61:69-90, 22 pgs.

Jin Z, et al., Midkine Enhances Soft-Tissue Sarcoma Growth: A Possible Novel Therapeutic Target, Clin. Cancer Res. 2008; 14:5033-42, 10 pgs.
Kobayashi S, et al., EGFR Mutation and Resistance of Non-Small-Cell Lung Cancer to Gefitinib, N. Engl. J. Med. 2005; 352:786-92, 7 pgs.
Kwak EL, et al., Anaplastic Lymphoma Kinase Inhibition in Non-Small-Cell Lung Cancer, N. Engl. J. Med. 2010; 363:1693-703, 11 pgs.
Maeda Y, et al., PARP-2 Interacts with TTF-1 and Regulates Expression of Surfactant Protein-B, J Biol Chem. 2006; 281:9600-6, 7 pgs.
Magnuson B., et al., Regulation and function of ribosomal protein S6 kinase (S6K) within mTOR signaling networks, (2012) Biochem J. 441:1-21, 21 pgs.
Maruyama K, et al., Midkine, a Heparin-Binding Growth Factor, Is Fundamentally Involved in the Pathogenesis of Rheumatoid Arthritis, Arthritis Rheum. 2004; 50:1420-9, 10 pgs.
Matsui T, et al., Midkine inhibitors: application of a simple assay procedure to screening of inhibitoiy compounds, Int. Arch. Med. 2010; 3:12, 5 pgs.
Miyauchi M, et al., Expression of Herpes Simplex Virus-Thymidine Kinase Gene Controlled by a Promoter Region of the Midkine Gene Confers Selective Cytotoxicity to Ganciclovir in Human Carcinoma Cells, Int. J. Cancer. 2001; 91:723-7, 5 pgs.
Morales, et al., Surfactants: their critical role in enhancing drug delivery to the lungs, Ther. Deliv., 2011, 2(5):623-641, 19 pgs.
Muramatsu T., Midkine and Pleiotrophn: Two Related Proteins Involved in Development, Survival, Inflammation and Tumorigenesis, J. Biochem. 2002; 132:359-71, 13 pgs.
Ogawa N, et al., Novel Combination Therapy for Human Colon Cancer with Adenovirus-Mediated Wild-Type p53 Gene Transfer and DNA-Damaging Chemotherapeutic Agent, Int. J. Cancer. 1997; 73:367-70, 4 pgs.
Owada K, et al., Midkine Inhibits Caspase-Dependent Apoptosis via the Activation of Mitogen-Activated Protein Kinase and Phosphatidylinositol 3-Kinase in Cultured Neurons, J. Neurochem. 1999; 73:2084-92, 9 pgs.
Perez-Moreno P, et al., Squamous Cell Carcinoma of the Lung: Molecular Subtypes and Therapeutic Opportunities, Clin. Cancer Res. 2012; 18:2443-51, 9 pgs.
Pubchem, Compound Summary for CID 15991416. Create date: Mar. 27, 2007, Retrieved from the Internet. <URL: https://pubchem.ncbi.nlm.nih.gov/compound/15991416#section=Biological-Test-Results >. XP002765727, 15 pgs.
Pubchem, Compound Summary for CID 15991417. Create date: Mar. 27, 2007, Retrieved from the Internet. <URL: https://pubchem.ncbi.nlm.nih.gov/compound/15991417#section=Depositor-Supplied-Patent-Identifiers >. XP002765729, 15 pgs.
Pubchem, Compound Summary for CID 16451693, create date: Jul. 30, 2007. Retrieved from the internet. <URL: https://pubchem.ncbi.nlm.nih.gov/compound/16451693,?from=summary>, 10 pgs.
Pubchem, Compound Summary for CID 4636717. Create date: Sep. 16, 2005, Retrieved from the Internet. <URL: http://pubchem.ncbi.nlm.nih.gov/summary/summary.cgi?cid-F4636717&from=compound>, 3 pgs.
Pubchem, Compound Summary for CID 4636718. Create date: Sep. 16, 2005, Retrieved from the Internet. <URL: https://pubchem.ncbi.nlm.nih.gov/compound/4636718#section=Top >. XP002765728, 15 pgs.
Salmond, R.S. et al., MAPK, Phosphatidylinositol 3-Kinase, and Mammalian Target of Rapamycin Pathways Converge at the Level of Ribosomal Protein S6 Phosporylation to Control Metabolic Signaling in SD8 T Cells, (2009) J Immunol 183:7388-7397, 13 pgs.
Schiller JH, et al. Comparison of Four Chemotherapy Regimens for Advanced Non-Small-Cell Lung Cancer, N. Engl. J. Med. 2002; 346:92-8, 7 pgs.
Shimada H, et al., Preoperative serum midkine concentration is a prognostic marker for esophageal squamous cell carcinoma, Cancer Science. 2003; 94:628-32, 5 pgs.
STN Registry Compound CAS No. 618391-40-5, Entered STN: Nov. 19, 2003, Supplier AKos Consulting and Solutions GmbH, STN search of Nov. 16, 2016, 1 pg.

(56) References Cited

OTHER PUBLICATIONS

STN Registry Compound CAS No. 618391-42-7, Entered STN: Nov. 19, 2003, Supplier AKos Consulting and Solutions GmbH, STN search of Nov. 16, 2016, 1 pg.
STN Registry Compound CAS No. 618391-44-9, Entered STN: Nov. 19, 2003, Supplier AKos Consulting and Solutions GmbH, STN search of Nov. 16, 2016, 2 pgs.
STN Registry Compound CAS No. 618391-46-1, Entered STN: Nov. 19, 2003, Supplier AKos Consulting and Solutions GmbH, STN search of Nov. 16, 2016, 1 pg.
STN Registry Compound CAS No. 618391-48-3, Entered STN: Nov. 19, 2003, Supplier AKos Consulting and Solutions GmbH, STN search of Nov. 16, 2016, 1 pg.
STN Registry Compound CAS No. 881970-33-8, Entered STN: Apr. 26, 2006, Supplier Otava, STN search of Nov. 16, 2016, 1 pg.
STN Registry Compound CAS No. 881970-49-6, Entered STN: Apr. 26, 2006, Supplier Otava, STN search of Nov. 16, 2016, 1 pg.
STN Registry Compound CAS No. 881970-80-5, Entered STN: Apr. 26, 2006, Supplier Otava, STN search of Nov. 16, 2016, 2 pgs.
STN Registry Compound CAS No. 881970-87-2, Entered STN: Apr. 26, 2006, Supplier Otava, STN search of Nov. 16, 2016, 1 pg.
STN Registry Compound CAS No. 881970-95-2, Entered STN: Apr. 26, 2006, Supplier Otava, STN search of Nov. 16, 2016, 1 pg.
STN Registry Compound CAS No. 881971-03-5, Entered STN: Apr. 26, 2006, Supplier Otava, STN search of Nov. 16, 2016, 1 pg.
Takei Y, et al., 5'-, 3'-Inverted Thymidine-Modified Antisense Oligodeoxynucleotide Targeting Midkine: Its Design and Application for Cancer Therapy, J. Biol. Chem. 2002;277:23800-6, 7 pgs.
Takeuchi K, et al., REI, ROS1 and ALK fusions in lung cancer, Nat. Med. 2012; 18:378-81, 4 pgs.
"Targeting the BCL-2 Family," In: Cancer Drug Design and Discovery, $2^{nd}$ Ed., S. Neidle (ed.), Sep. 2013, p. 370, 2 pgs.
Tomizawa M, et al., A promoter region of the midkine gene that is frequently expressed in human hepatocellular carcinoma can activate a suicide gene as effectively as the α-fetoprotein promoter, Br. J. Cancer 2003; 89:1086-90, 5 pgs.
Tsutsui J, et al., A New Family of Heparin-binding Growth/Differentiation Factors: Increased Midkine Expression in Wilms' Tumor and Other Human Carcinomas, Cancer Res. 1993;53:1281-5, 5 pgs.
Webb D.R., Animal models of human disease: Inflammation, Biochemical Pharmacology 2014, 87, 121-130, 10 pgs.
Zakowski MF, et al., EGFR Mutations in Small-Cell Lung Cancers in Patients Who Have Never Smoked, N. Engl. J. Med. 2006; 355:213-5, 3 pgs.
European Search Report, Supplementary, and Written Opinion dated Jan. 27, 2017 for Application No. EP 14814014.8, 8 pgs.
European Search Report, Supplementary Partial, and Written Opinion dated Jun. 8, 2020 for Application No. EP 17835328.0, 10 pgs.
International Search Report and Written Opinion dated Oct. 20, 2017 for Application No. PCT/US2017/044335, 12 pgs.
International Search Report and Written Opinion dated Dec. 10, 2014 for Application No. PCT/US2014/043029, 17 pgs.
U.S. Office Action, Non-Final, dated Dec. 2, 2016 for U.S. Appl. No. 14/897,539, 15 pgs.
U.S. Appl. No. 61/837,436, filed Jun. 20, 2013.
U.S. Appl. No. 62/367,832, filed Jul. 28, 2016.
Takagi-Kimura, M., et al., "Enhanced antitumor efficacy of fiber-modified, midkine promoter-regulated oncolytic adenovirus in human malignant mesothelioma," Cancer Science, 2013, 104(11):1433-1439, 7 pgs.
Japanese Office Action, Notice of Reasons for Refusal, dated Apr. 27, 2021 for Application No. JP 2019-503470, 5 pgs.
European Examination Report dated Jul. 2, 2021 for Application No. EP 17835328.0, 5 pgs.
Japanese Office Action, Decision of Rejection, dated Sep. 21, 2021 for Application No. JP 2019-503470, 3 pgs.

|  | - | + | ++ | +++ |
|---|---|---|---|---|
| adenocarcinoma | 10 (25.0) | 10 (25.0) | 7 (17.5) | 13 (32.5) |
| squamous cell carcinoma | 14 (35.0) | 8 (20.0) | 8 (20.0) | 10 (25.0) |
| malignant pleural mesothelioma | 4 (19.1) | 7 (33.3) | 6 (28.5) | 4 (19.1) |

A

B

C

F4

A5

F5

F6

B5

D5

F2

E5

METHODS AND COMPOSITIONS FOR TREATING MESOTHELIOMA AND SMALL LUNG CANCER THAT EXPRESS MIDKINE

RELATED APPLICATIONS

This application claims the benefit of U.S. application Ser. No. 16/857,285 filed Apr. 24, 2020, entitled "Methods and Compositions for Treating Mesothelioma and Small Lung Cancer that Express Midkine," which claims the benefit of U.S. application Ser. No. 16/312,478 filed Dec. 21, 2018, entitled "Methods and Compositions for Treating Mesothelioma and Small Lung Cancer that Express Midkine," which claims the benefit of International Application No. PCT/US2017/044335 filed Jul. 28, 2017 entitled "Methods and Compositions to Treat Cancer," which claims the benefit of U.S. Provisional Application No. 62/367,832 filed Jul. 28, 2016 entitled "Role of Midkine Inhibitors in Malignant Pleural Mesothelioma" which are incorporated herein by reference in their entirety for all purposes.

BACKGROUND OF THE INVENTION

Malignant pleural mesothelioma is an aggressive tumor of mesenchymal origin and is increasing worldwide as a result of widespread exposure to asbestos. The median survival of patients with mesothelioma from time of diagnosis ranges between 1 and 2 years. The mortality is expected to increase, at least until 2020, which is mainly due to the long latency (30-50 years) of the disease. Despite considerable advances in the understanding of its pathogenesis and etiology, malignant mesothelioma remains largely unresponsive to standard modalities of cancer therapy. Thus, there is an urgent need for new therapeutic options for mesothelioma.

SUMMARY OF THE INVENTION

Embodiments provided herein relate to methods and compositions for treating mesothelioma and/or a small cell lung cancer that express midkine.

DETAILED DESCRIPTION

Figure 1:
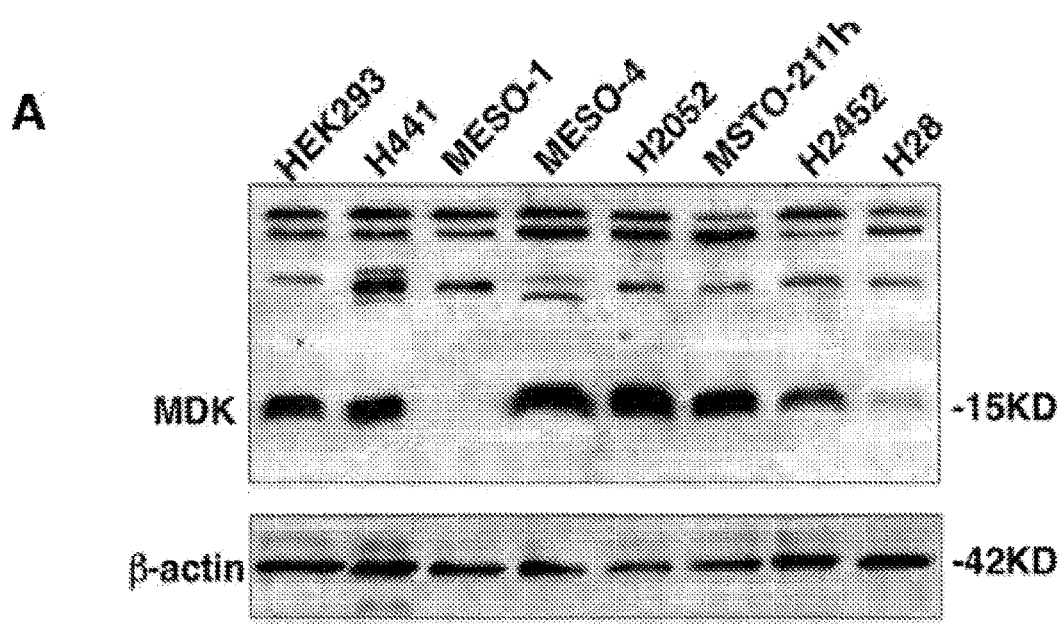
FIG. 1. Midkine is commonly expressed in human malignant pulmonary mesothelioma. A. Immunoblot analysis of MDK in indicated cells. B. MDK expression in primary pulmonary adenocarcinoma samples of 40 patients, lung squamous cell lung cancer samples of 40 patients and 22 malignant pulmonary mesothelioma who underwent surgical tumor resection. Percentage values are given in parentheses.
Figure 1:
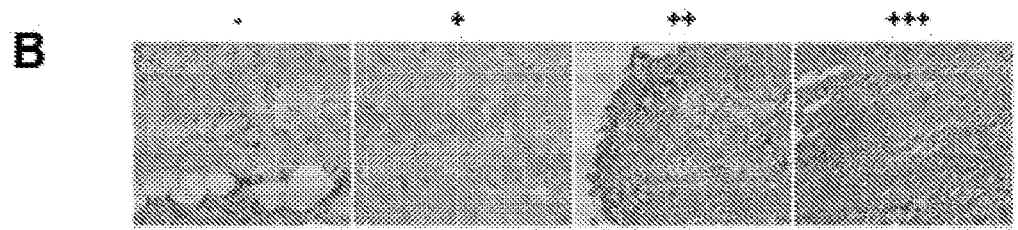
Figure 2:
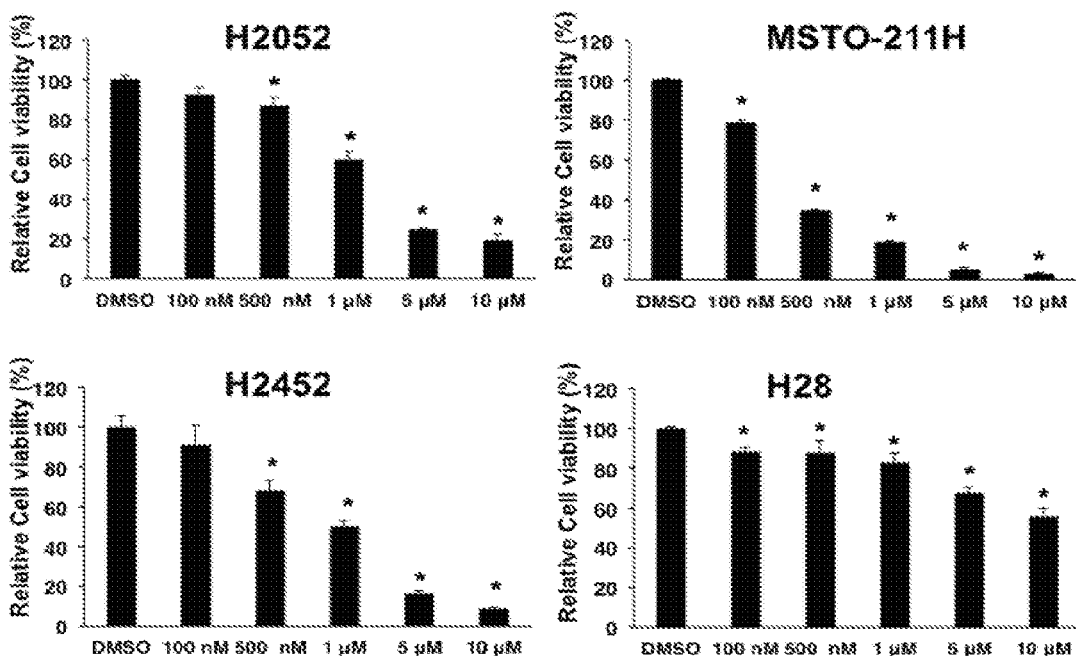
FIG. 2. iMDK suppressed cell viability of MDK expressing malignant pulmonary mesothelioma cells. Dose-dependent growth inhibition by iMDK was observed in the MDK-positive H2052, MSTO-211H, H2452 and H28 mesothelioma cells after 48 hours of treatment. Cell viability was assessed by trypan blue exclusion assay. Statistical significance was defined as $p<0.01$ (*).
Figure 3:
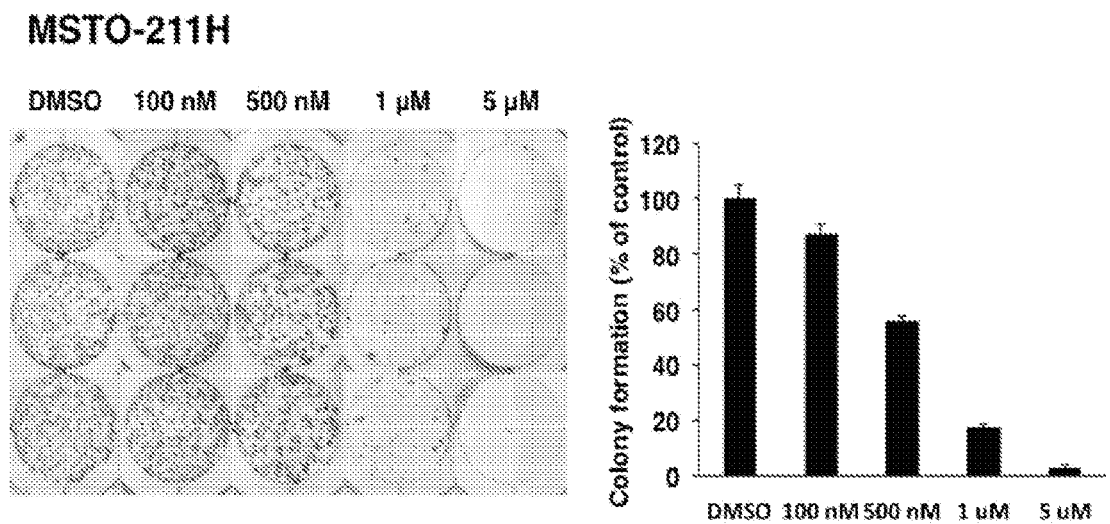
FIG. 3. iMDK suppressed colony formation of malignant pulmonary mesothelioma cells. Colony formation of MSTO-211H cells treated with iMDK. Fourteen days after the treatment, cells were fixed and stained with crystal violet. Representative images of experiments performed in triplicate are shown.
Figure 4:
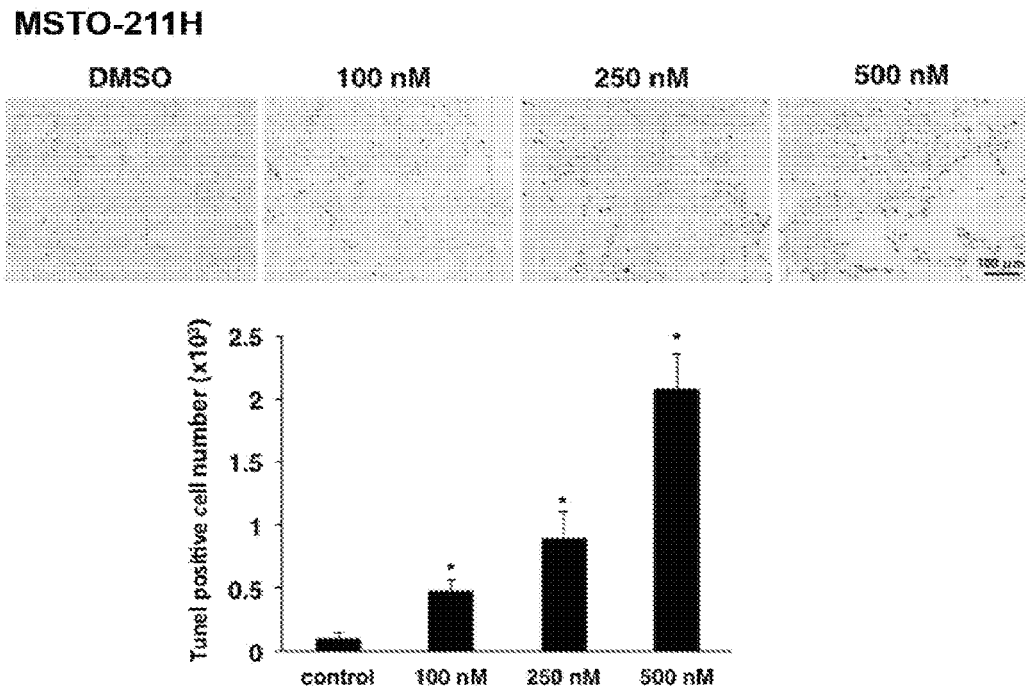
FIG. 4. iMDK induced apoptosis malignant pulmonary mesothelioma cells. Cells were treated for 48 h at a indicated concentration of iMDK then TUNEL staining was performed to detect apoptosis using the DeadEnd colorimetric TUNEL system (Promega, Madison, Wis.) according to the manufacturer's protocol. Statistical significance was defined as $p<0.01$ (*).
Figure 5:
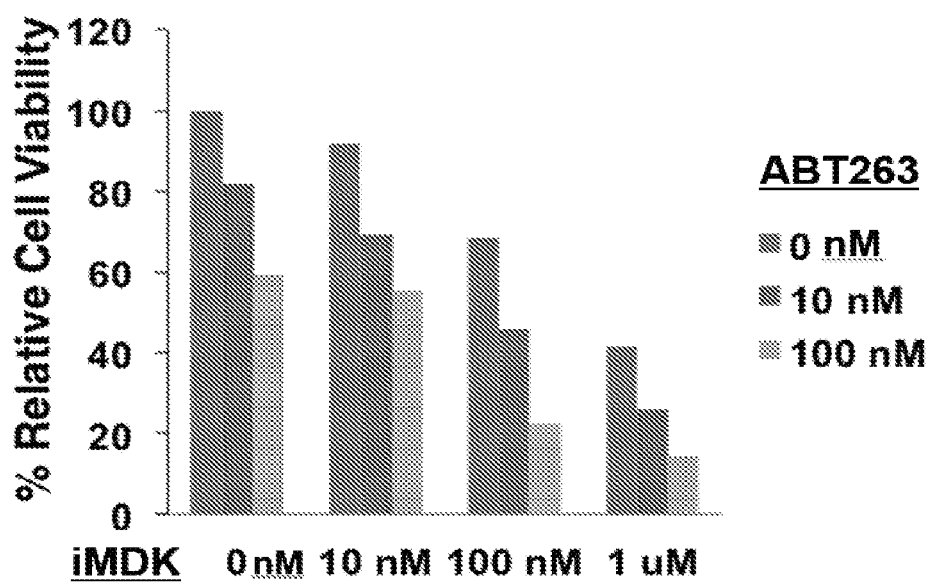
FIG. 5. ABT263 enhanced iMDK-mediated suppression of cell proliferation in MSTO-211H mesothelioma cells. ABT263 enhanced growth inhibition in MSTO-211H cells after 48 hours of treatment.
Figure 6:
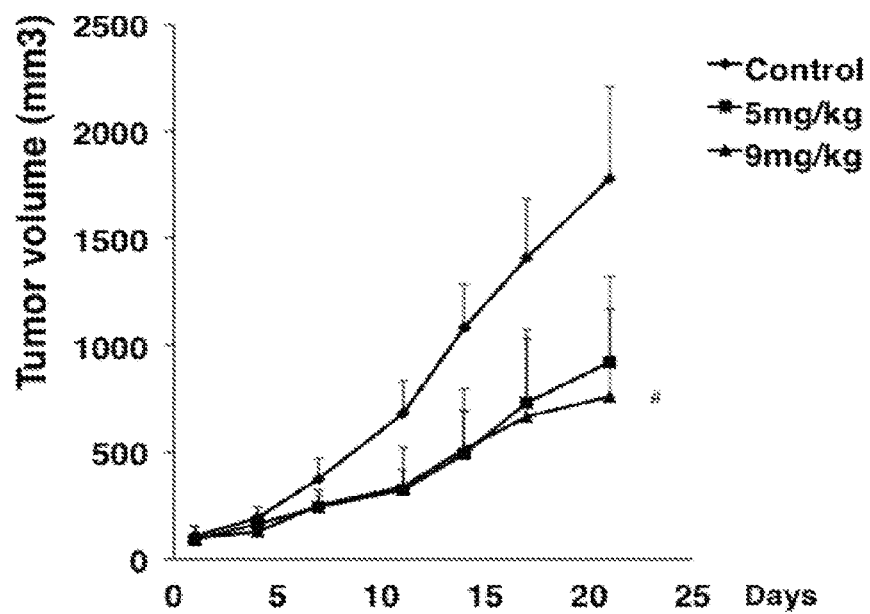
FIG. 6. iMDK effectively reduced malignant pleural mesothelioma growth in a xenograft mouse model. Volume of the tumors derived from MSTO-211H cells was significantly reduced after the treatment with iMDK (9 mg/kg, i.p.) and iMDK (5 mg/kg, i.p.) compared control (DMSO) in a xenograft mouse model. Eight mice were used in each group. Tumor growth is expressed as mean tumor volume; bars represent SD. Statistical significance was defined as $p<0.05$ (#)
Figure 7:
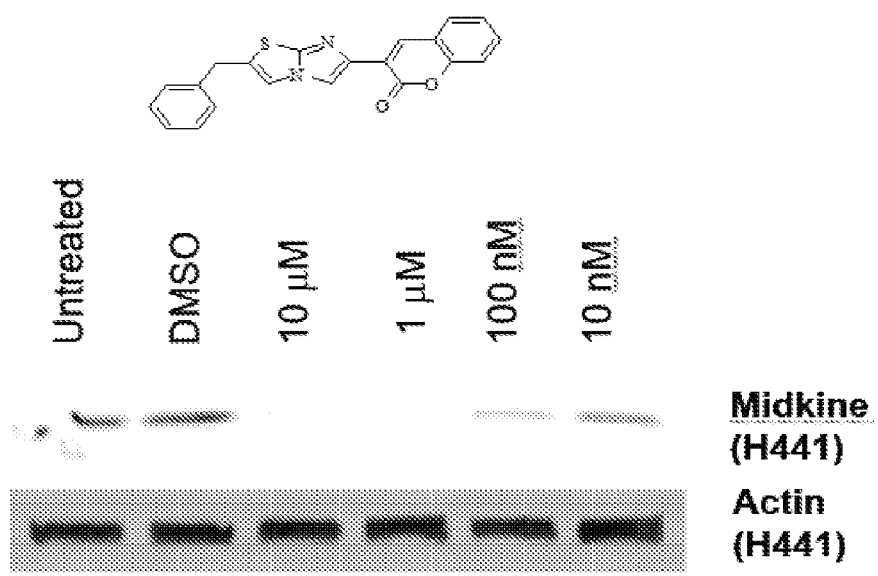
FIG. 7. Activity of Compound 5 on protein expression. 1 uM of Compound 5 inhibits protein expression FIG. 8. Activity of Compound 9 on protein expression. 1 uM of Compound 9 inhibits protein expression.
Figure 8:
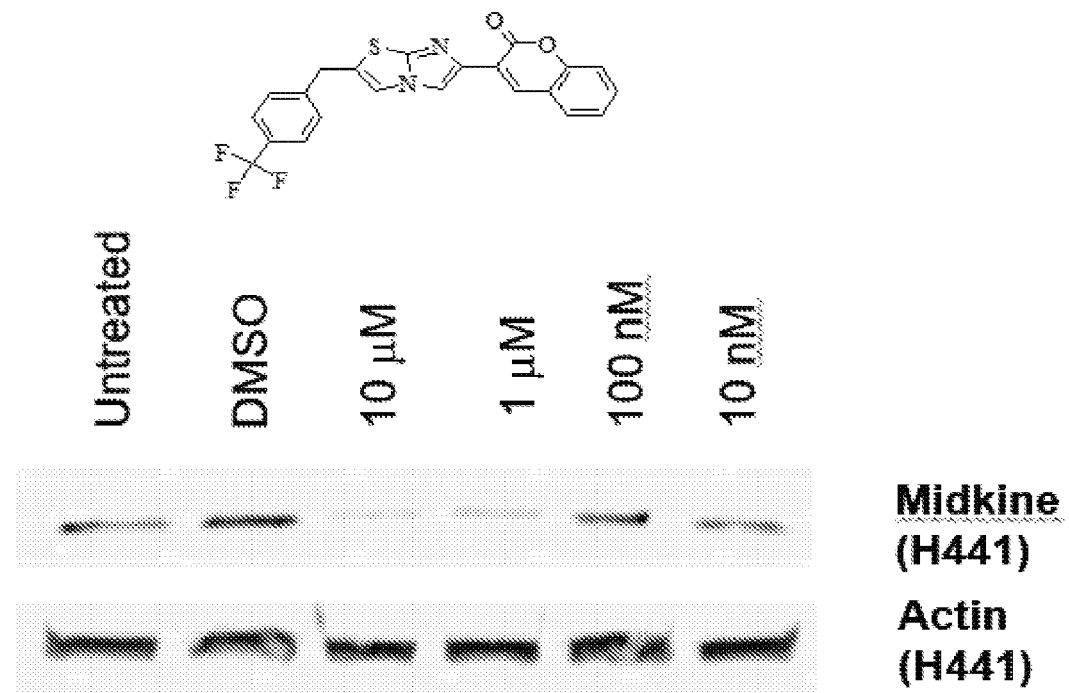
Figure 9:
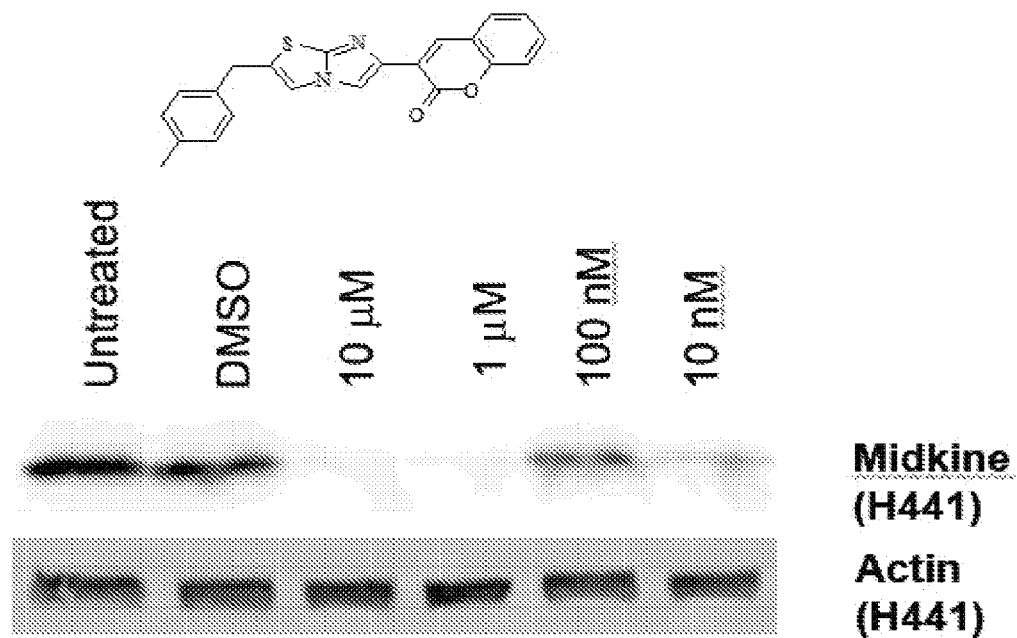
FIG. 9. Activity of Compound 8 on protein expression. 1 uM of Compound 8 inhibits protein expression.
Figure 10:
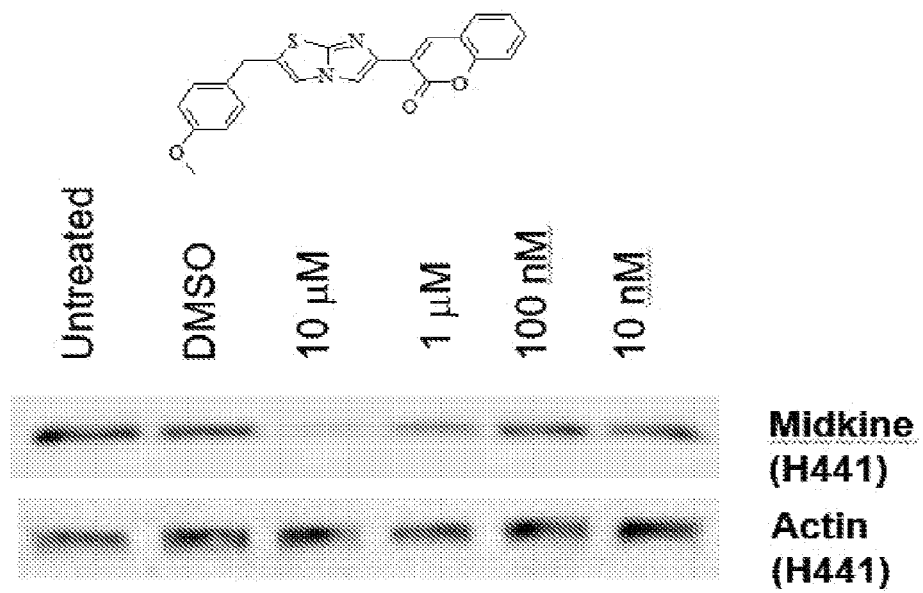
FIG. 10. Activity of Compound 6 on protein expression. 1 uM of Compound 6 inhibits protein expression.
Figure 11:
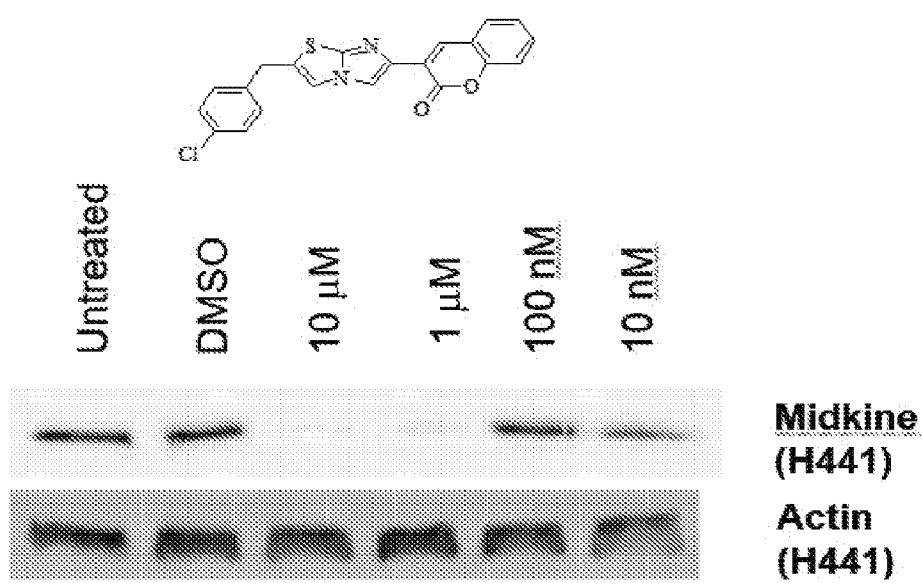
FIG. 11. Activity of Compound 1 on protein expression. 1 uM of Compound 1 inhibits protein expression.
Figure 12:
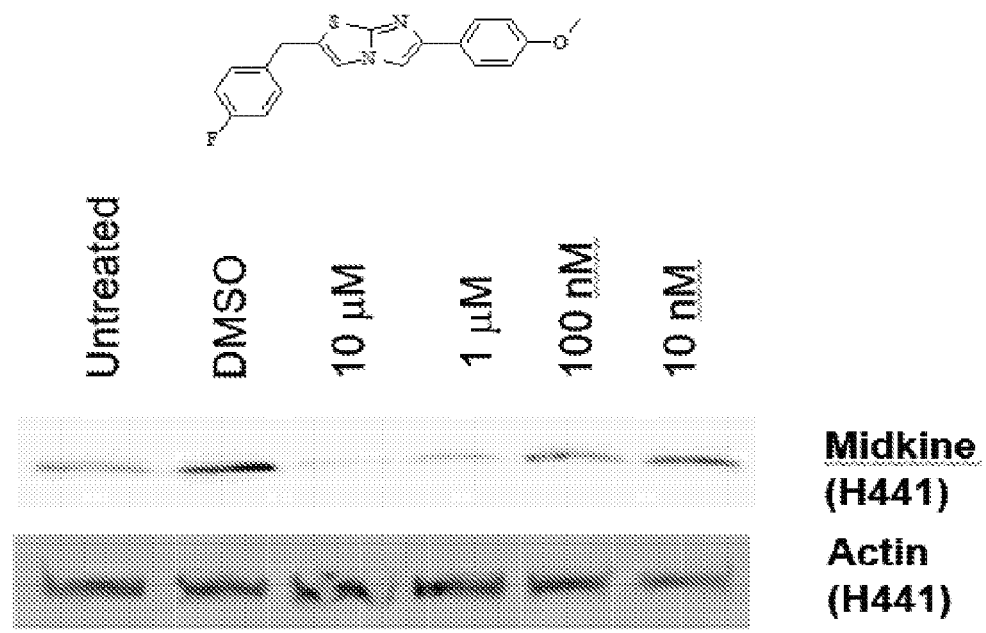
FIG. 12. Activity of Compound 10 on protein expression. 1 uM of Compound 10 inhibits protein expression.
Figure 13:
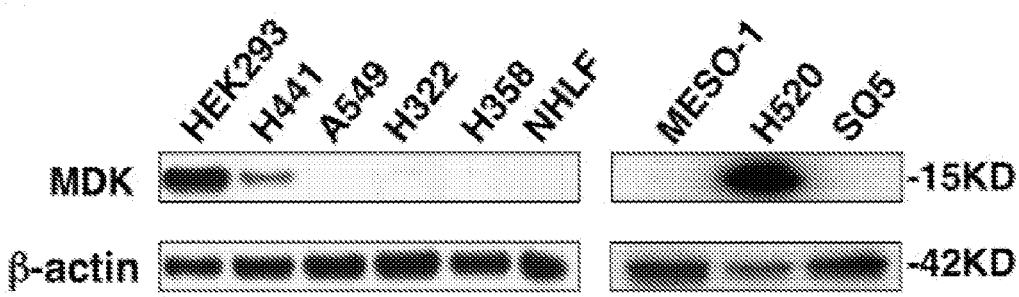
FIG. 13. Detection of MDK Expression in MPM cells and NCSLC cells by immunoblot analysis. Growth inhibition was increased by the MDK knockdown in H441 lung adenocarcinoma cells. MDK was detected in HEK293 cells, H441 lung adenocarcinoma cells and H520 human lung squamous cell carcinoma cells but not in the other kinds of cells including NHLF (Normal Human Lung Fibroblast) cells. Protein expression of MDK and µ-actin was confirmed by immunoblot as described in Methods. A. MDK was suppressed by two different MDK siRNAs (MDK siRNA1 and MDK siRNA2) in H441 cells. Protein expression was confirmed by immunoblot as described in A. B. Growth inhibition in H441 cells after MDK gene silencing was significantly increased. Cell viability was assessed by trypan blue exclusion assay as described in Methods. Statistical significance was defined as $p<0.01$ (*).
Figure 13:
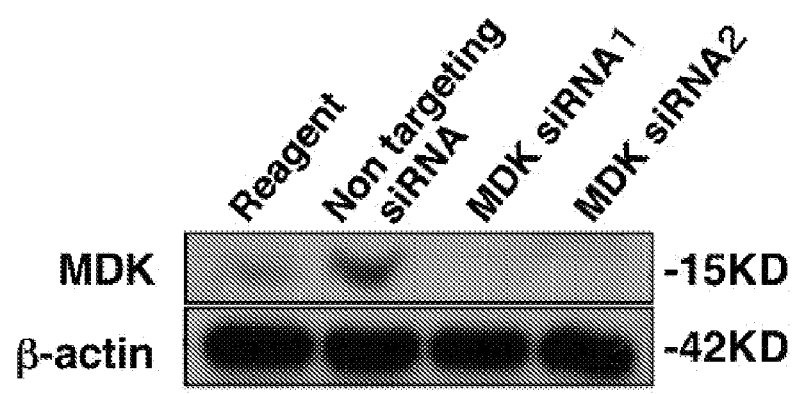
Figure 13:
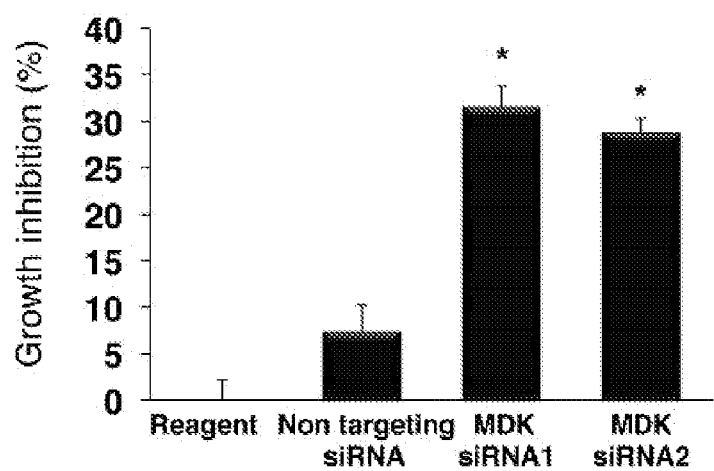
Figure 14:
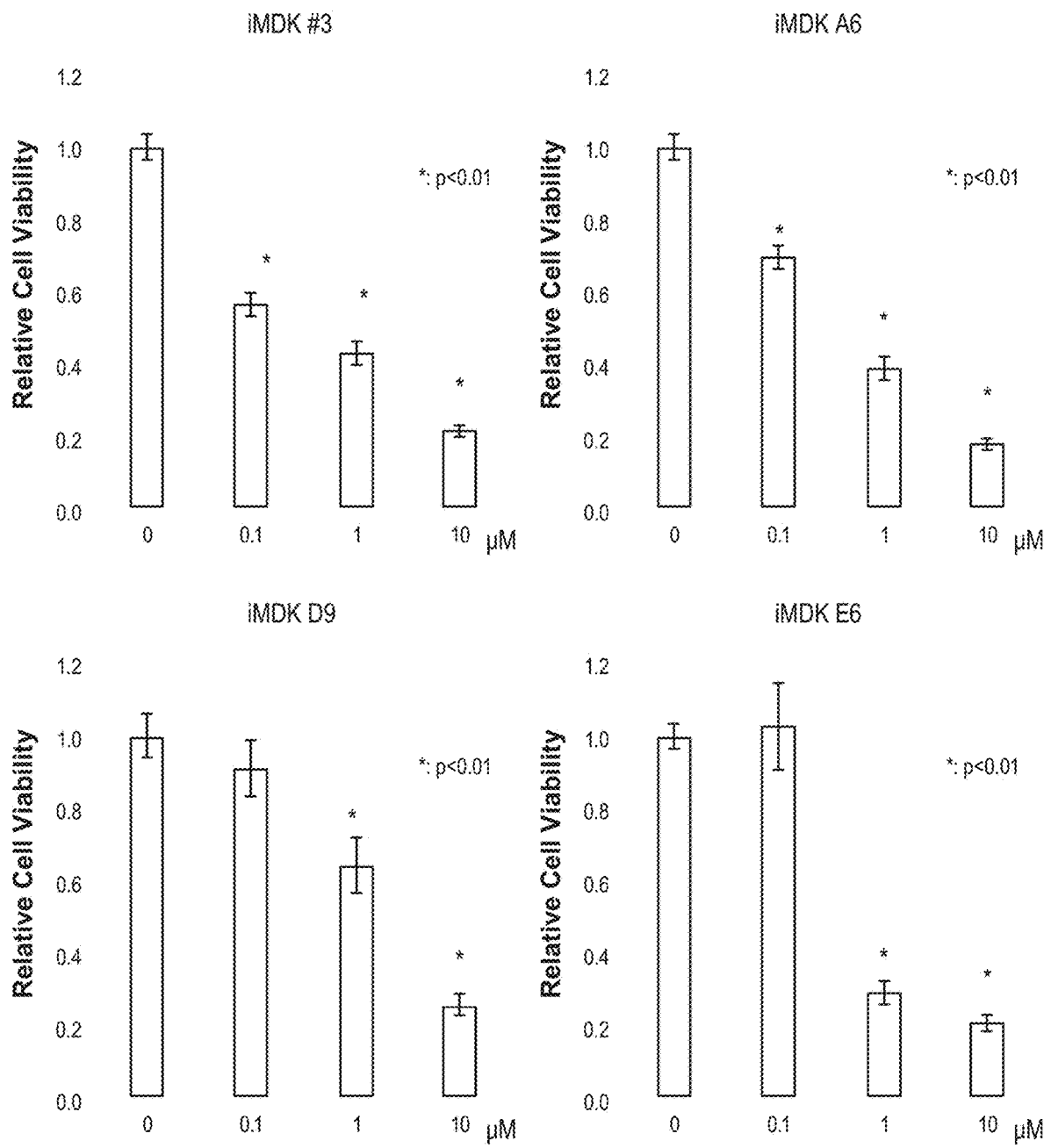
FIG. 14. iMDK (#3) and its derivatives (A6, D9 and E6) inhibits growth of MSTO211H mesothelioma cells. MSTO211H mesothelioma cells were treated with iMDK (#3) or iMDK derivatives (A6, D9 or E6) at indicated different final concentrations. Forty-eight hours after treatment, number of cells was counted using Countess II (Themo Fisher Scientific). iMDK and iMDK derivatives significantly inhibited the growth of MSTO211H cells in a dose-dependent manner. *, $p<0.05$ (Student t-test; triplicate samples) was considered significant compared to DMSO control (0 µM).
Figure 15:
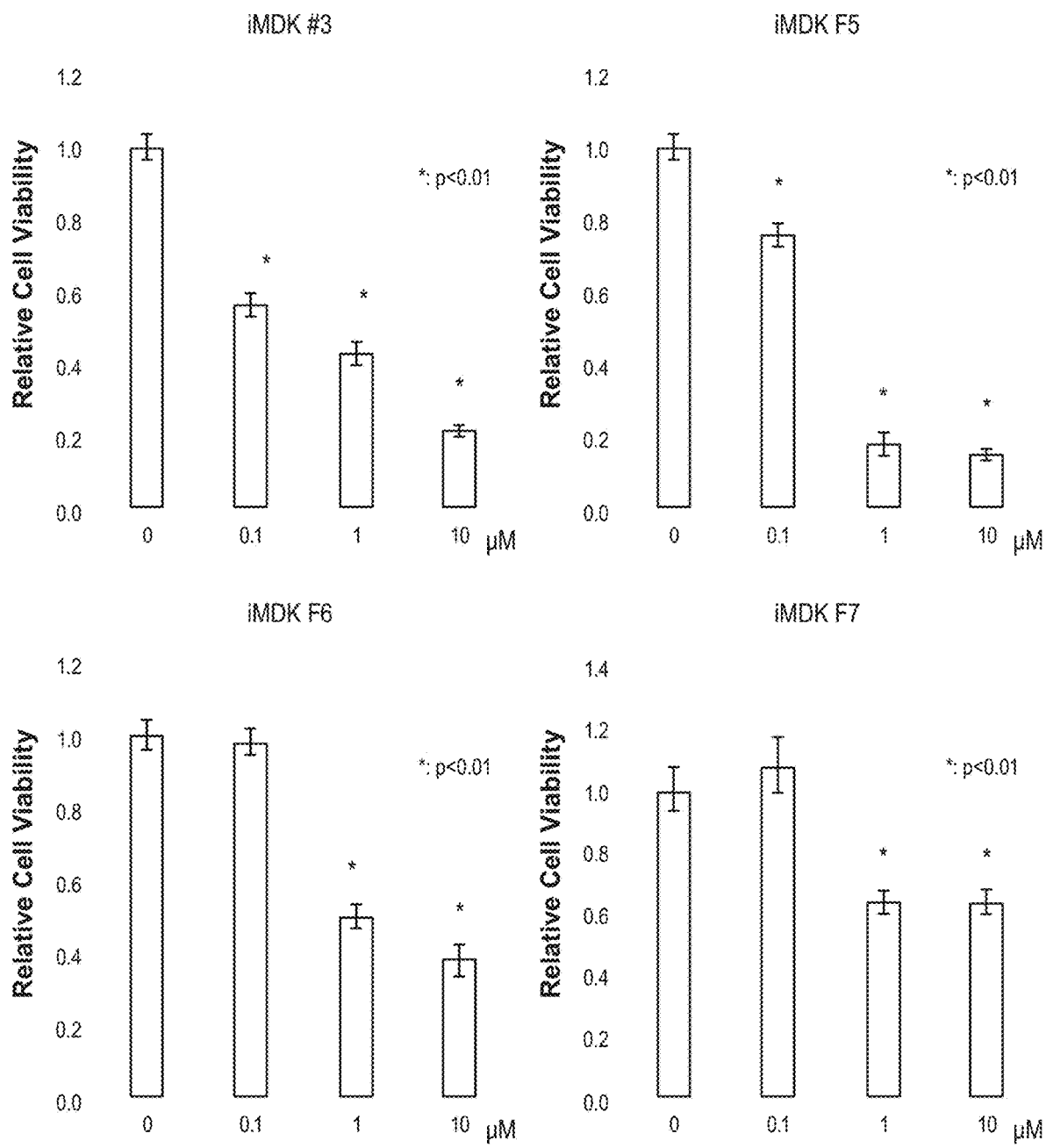
FIG. 15. iMDK (#3) and its derivatives (F5, F6 and F7) inhibits growth of MSTO211H mesothelioma cells. MSTO211H mesothelioma cells were treated with iMDK (#3) or iMDK derivatives (F5, F6 or F7) at indicated different final concentrations. Forty-eight hours after treatment, number of cells was counted using Countess II (Themo Fisher Scientific). iMDK and iMDK derivatives significantly inhibited the growth of MSTO211H cells in a dose-dependent manner. *, $p<0.05$ (Student t-test; triplicate samples) was considered significant compared to DMSO control (0 µM).
Figure 16:
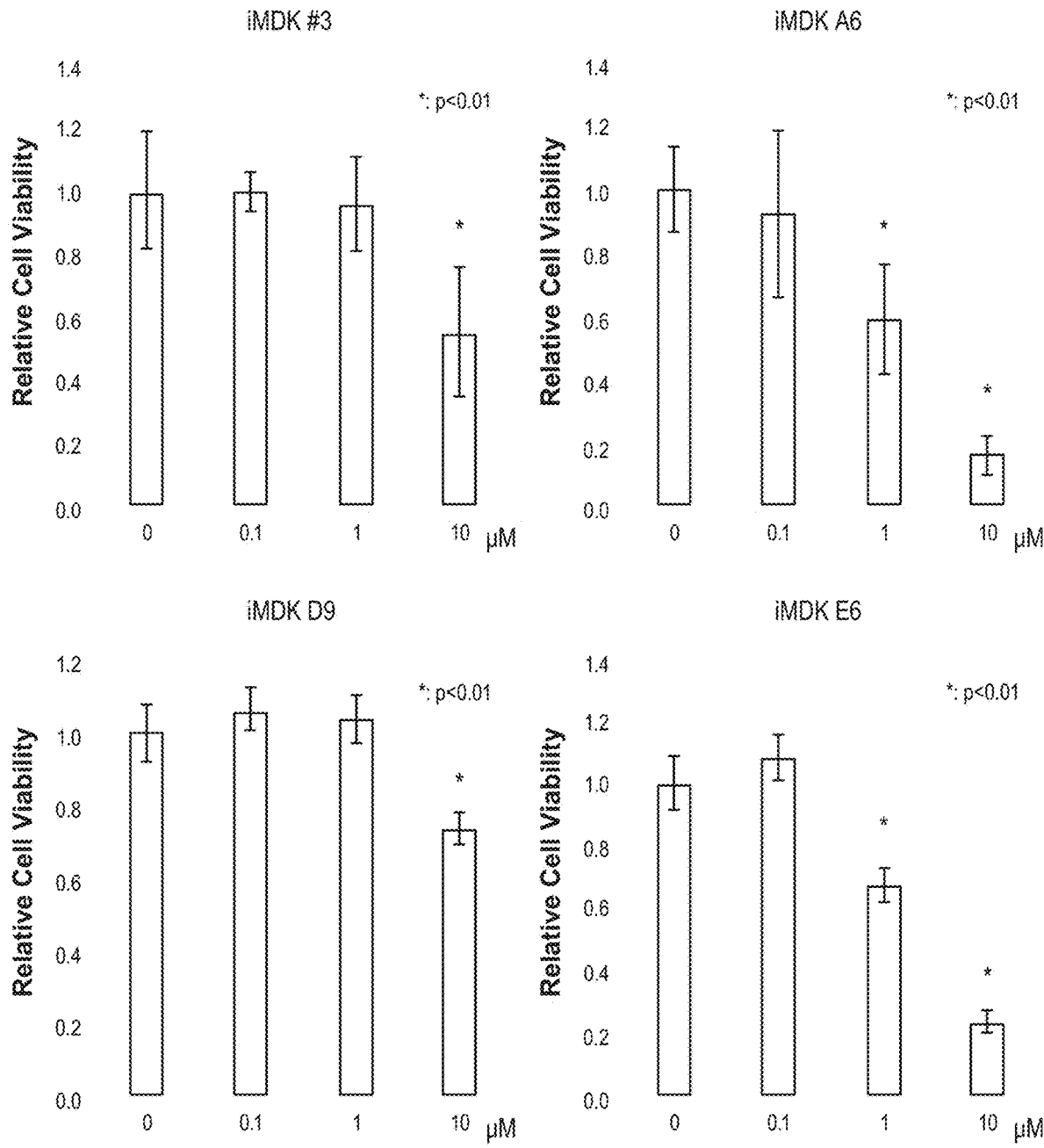
FIG. 16. iMDK (#3) and its derivatives (A6, D9 and E6) inhibits growth of MESO4 mesothelioma cells. MESO4 mesothelioma cells were treated with iMDK (#3) or iMDK derivatives (A6, D9 or E6) at indicated different final concentrations. Forty-eight hours after treatment, number of cells was counted using Countess II (Themo Fisher Scientific). iMDK and iMDK derivatives significantly inhibited the growth of MESO4 cells in a dose-dependent manner. *, $p<0.05$ (Student t-test; triplicate samples) was considered significant compared to DMSO control (0 μM).
Figure 17:
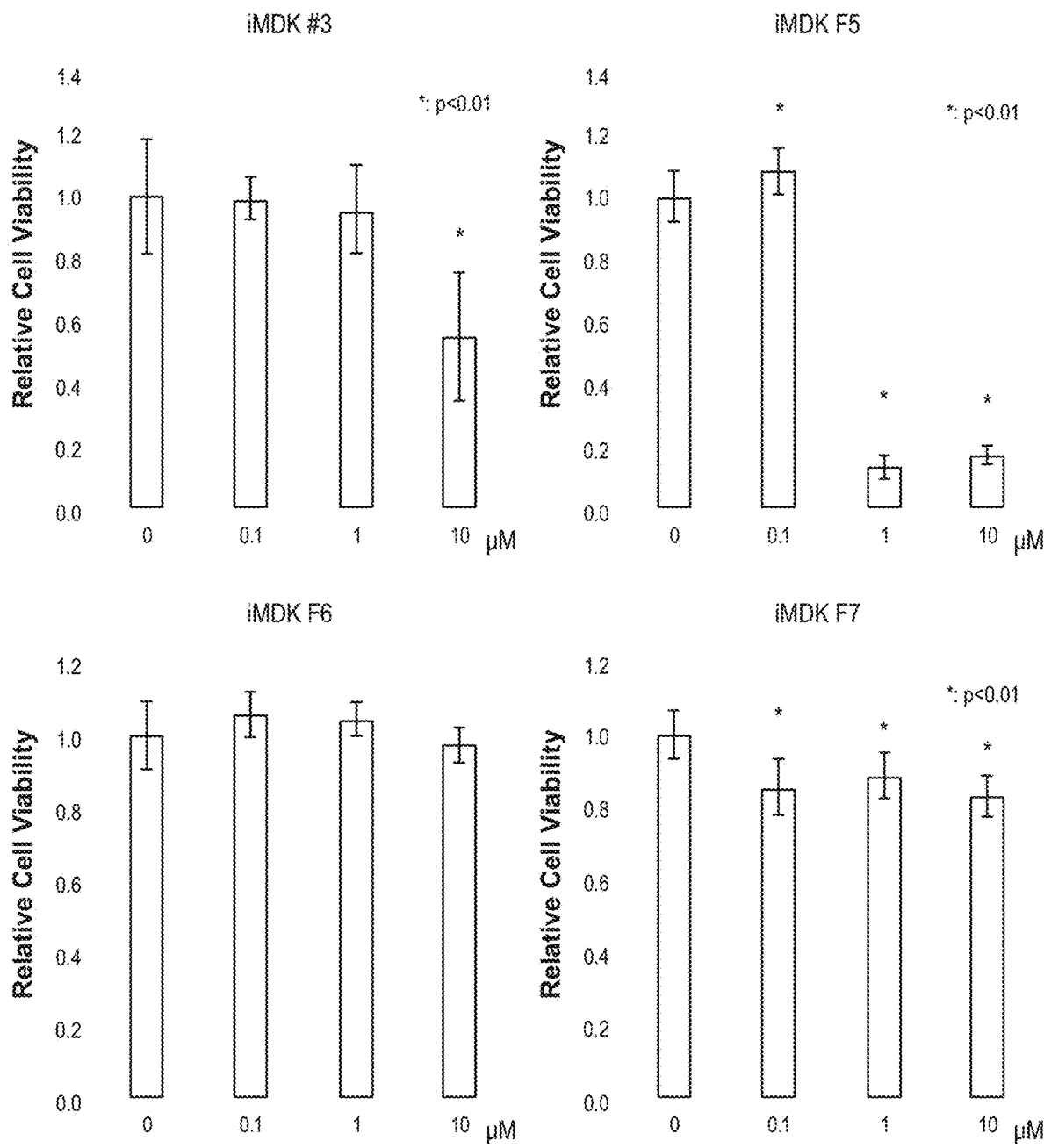
FIG. 17. iMDK (#3) and its derivatives (F5, F6 and F7) inhibits growth of MSTO211H mesothelioma cells. MESO4 mesothelioma cells were treated with iMDK (#3) or iMDK derivatives (F5, F6 or F7) at indicated different final concentrations. Forty-eight hours after treatment, number of cells was counted using Countess IT (Themo Fisher Scientific). iMDK and iMDK derivatives significantly inhibited the growth of MESO4 cells in a dose-dependent manner. *, $p<0.05$ (Student t-test; triplicate samples) was considered significant compared to DMSO control (0 μM).
Figure 18:
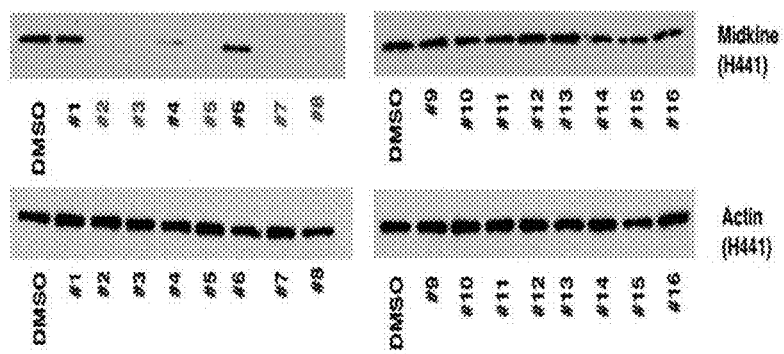
FIG. 18. Compounds #2 (also known as F6), #3 (also known as iMDK), #5, #7, and #8 also suppressed endogenous midkine expression in H441 lung adenocarcinoma cells. A. H441 lung adenocarcinoma cells were treated with iMDK and related compounds at a final concentration of 10 μM. Twenty-four hours after treatment, cells were harvest and protein expression was assessed using western blotting assay. These compounds may inhibit the expression of midkine expressed in mesothelioma cells as well, which suggest that these compounds can be used to treat mesothelioma. B. Shown is structures of compounds #2 (also known as F6), #3 (also known as iMDK), #5, #7, and #8. C. Wright-Giemsa staining of 293 cells 3 days after treatment (10 μM) shows that compounds #2 (also known as F6), #3 (also known as iMDK), #5, #7, and #8 inhibited cell viability of H441 cells (not shown here) and 293 cells (shown). DMSO was used as control.
Figure 18:
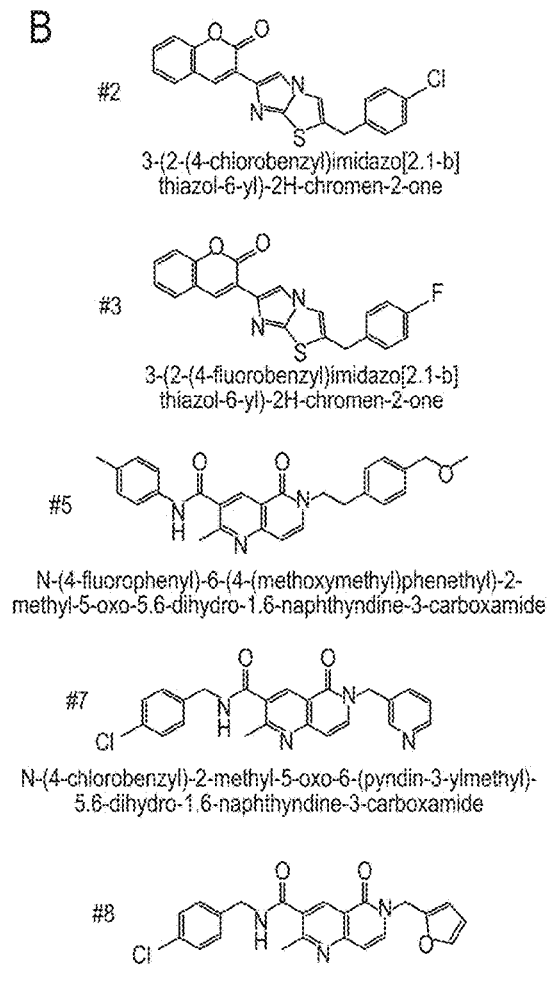
Figure 18:
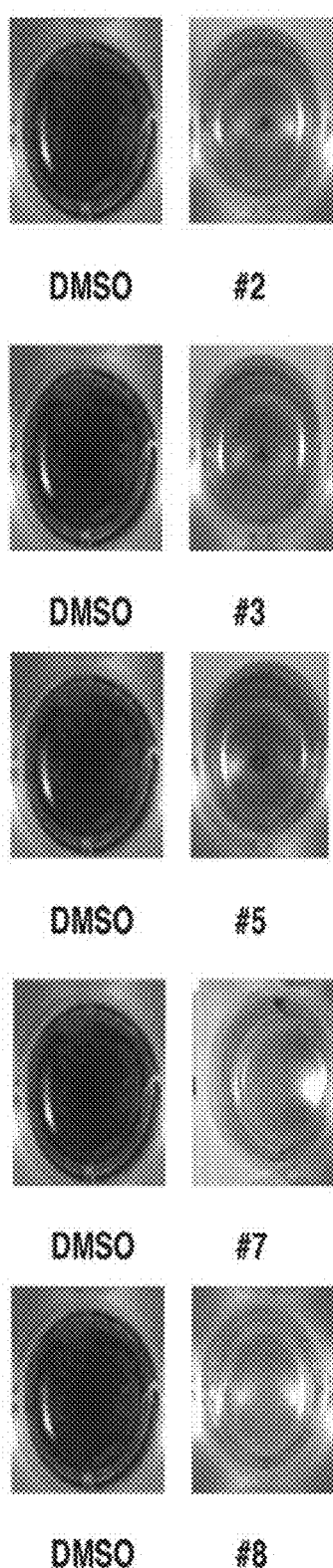
Figure 19:
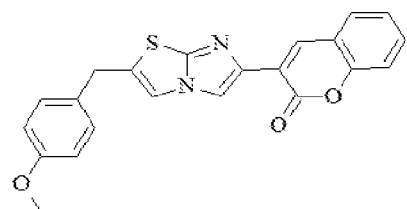
FIG. 19. Compounds found to be toxic to H441 cells. These compounds are likely to be toxic to mesothelioma cells as well.
Figure 19:
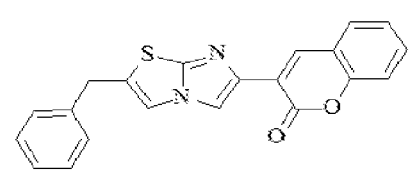
Figure 19:
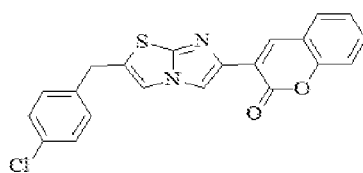
Figure 19:
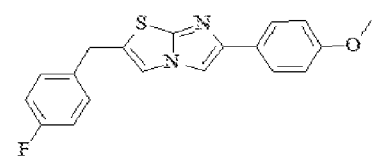
Figure 19:
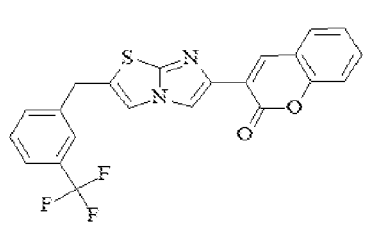
Figure 19:
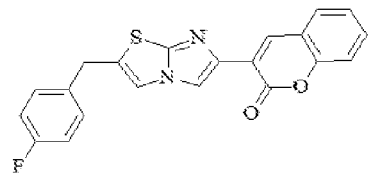
Figure 19:
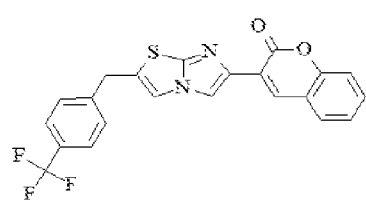
Figure 19:
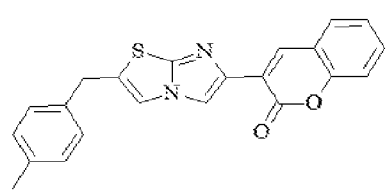

As used herein and in the appended claims, the singular forms "a," "and," and "the" include plural referents unless the context clearly dictates otherwise. Thus, for example, reference to "a method" includes a plurality of such methods and reference to "a dose" includes reference to one or more doses and equivalents thereof known to those skilled in the art, and so forth.

The term "about" or "approximately" means within an acceptable error range for the particular value as determined by one of ordinary skill in the art, which will depend in part on how the value is measured or determined, e.g., the limitations of the measurement system. For example, "about" can mean within 1 or more than 1 standard deviations, per the practice in the art. Alternatively, "about" can mean a range of up to 20%, or up to 10%, or up to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed.

"Dosage unit form" as used herein refers to physically discrete units suited as unitary dosages for the subject to be treated, each unit containing a predetermined quantity of active compound calculated to produce the desired therapeutic effect in association with the required pharmaceutical carrier. The specification for the dosage unit forms of the preferred embodiments are dictated by and directly dependent on the unique characteristics of the active compound and the particular therapeutic effect to be achieved, and the limitations inherent in the art of compounding such an active compound for the treatment of individuals.

The terms "individual," "host," "subject," and "patient" are used interchangeably to refer to an animal that is the object of treatment, observation and/or experiment. "Animal" includes vertebrates and invertebrates, such as fish, shellfish, reptiles, birds, and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans.

As used herein the language "pharmaceutically acceptable carrier" is intended to include any and all solvents, dispersion media, coatings, antibacterial and antifungal agents, isotonic and absorption delaying agents, and the like, compatible with pharmaceutical administration. Pharmaceutically acceptable carriers include a wide range of known diluents (i.e., solvents), fillers, extending agents, binders, suspending agents, disintegrates, surfactants, lubricants, excipients, wetting agents and the like commonly used in this field. These carriers may be used singly or in combination according to the form of the pharmaceutical preparation, and may further encompass "pharmaceutically acceptable excipients" as defined herein.

As used herein, "pharmaceutically acceptable excipient" means any other component added to a pharmaceutical formulation other than the active ingredient and which is capable of bulking-up formulations that contain potent active ingredients (thus often referred to as "bulking agents," "fillers," or "diluents") to allow convenient and accurate dispensation of a drug substance when producing a dosage form. Excipients may be added to facilitate manufacture, enhance stability, control release, enhance product characteristics, enhance bioavailability drug absorption or solubility, or other pharmacokinetic considerations, enhance patient acceptability, etc. Pharmaceutical excipients include, for example, carriers, fillers, binders, disintegrants, lubricants, glidants, colors, preservatives, suspending agents, dispersing agents, film formers, buffer agents, pH adjusters, preservatives etc. The selection of appropriate excipients also depends upon the route of administration and the dosage form, as well as the active ingredient and other factors, and will be readily understood by one of ordinary skill in the art.

As used herein, the term "therapeutically effective amount" means the total amount of each active component of the pharmaceutical composition or method that is sufficient to show a meaningful patient benefit, e.g., healing of chronic conditions or in an increase in rate of healing of such conditions, or in a reduction in aberrant conditions. This includes both therapeutic and prophylactic treatments. Accordingly, the compounds can be used at very early stages of a disease, or before early onset, or after significant progression. When applied to an individual active ingredient, administered alone, the term refers to that ingredient alone. When applied to a combination, the term refers to combined amounts of the active ingredients that result in the therapeutic effect, whether administered in combination, serially or simultaneously.

Midkine (MDK) is a heparin-binding growth factor that is highly expressed in many malignant tumors, including lung cancers. We have previously reported that a MDK inhibitor, iMDK, suppresses non-small cell lung cancer expressing MDK without harming normal cells. Importantly, iMDK inhibits the PI3 kinase/Akt pathway and induces apoptosis in MDK expressing non-small cell lung cancer cells. In the present study, we have investigated the anti-tumor effect of iMDK against malignant mesothelioma both in vitro and in vivo. 48 hours after treatment, iMDK dose-dependently inhibited cell growth of MDK expressing malignant mesothelioma cells. iMDK also suppressed colony formation of MSTO-211H mesothelioma cells. TUNEL positive cells were significantly increased in MSTO-211H cells 48 hours after iMDK treatment in a dose dependent manner, confirming the induction of apoptosis in mesothelioma cells by iMDK. Combination treatment of iMDK and Bcl-2 inhibitor ABT-263 is more effective than each drug alone in MSTO-211H mesothelioma cells. Moreover, systemic administration of iMDK significantly inhibited tumor growth in a mesothelioma xenograft tumor in vivo. Inhibition of MDK with iMDK provides a potential therapeutic approach for the treatment of malignant mesothelioma that is driven by MDK.

Disclosed herein are low molecular weight compounds, including "iMDK" that suppress endogenous MDK expression. In one aspect, disclosed are methods of treating malignant mesothelioma and/or a small cell lung cancer that express midkine. The methods may comprise the step of administering to an individual in need thereof, an effective amount of a pharmaceutical composition comprising a compound of formula (I) and a pharmaceutical carrier, wherein formula (I) may be:

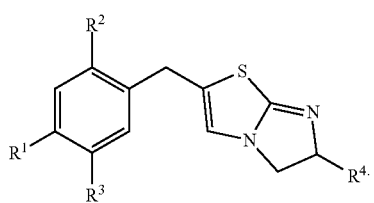
(I)

or a pharmaceutically acceptable salt thereof, wherein:
$R^1$ may be hydrogen, —OCH$_3$, —CH$_3$, —CF$_3$ or halogen;
$R^2$ may be hydrogen or chlorine;
$R^3$ may be hydrogen, chlorine or —CF$_3$; and

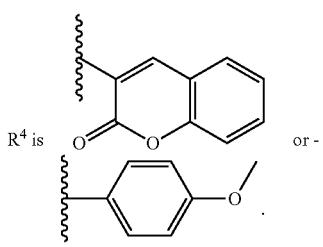

In one aspect,
$R^1$ may be hydrogen or halogen;
$R^2$ may be hydrogen or chlorine;
$R^3$ may be hydrogen or chlorine, when $R^1$ is hydrogen then $R^2$ and $R^3$ are chlorine, and when $R^2$ and $R^3$ are chlorine then $R^1$ is hydrogen.

In one aspect, $R^1$ may be selected from hydrogen, —OCH$_3$ and halogen; and $R^2$ and $R^3$ are hydrogen.

In one aspect, $R^1$ may be fluorine.

In one aspect, formula (I) may be selected from the group consisting of:

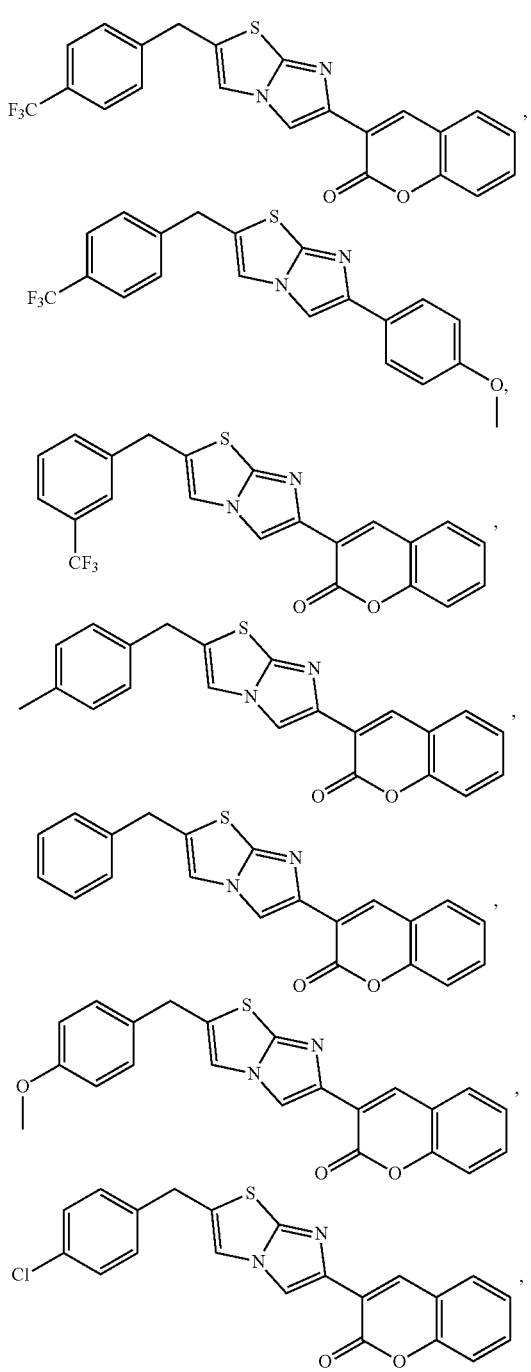

-continued
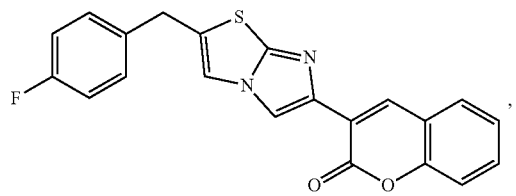
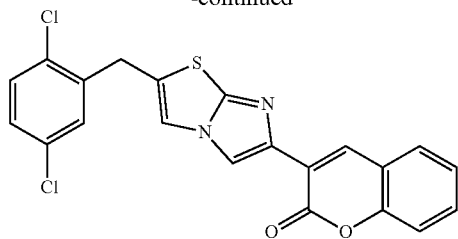
In one aspect, wherein formula (I) may be:
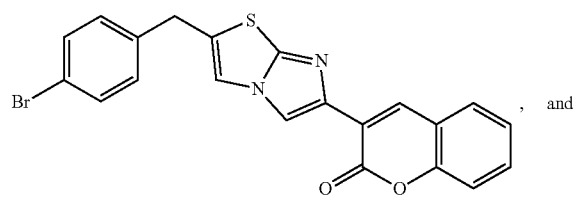
, and
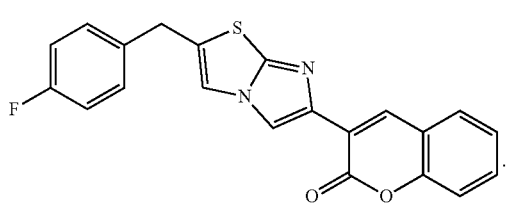 [SMILES: O=c1oc2ccccc2cc1-c1cn2cc(Cc3ccc(F)cc3)sc2n1]
.
In one aspect, wherein formula (I) may be:
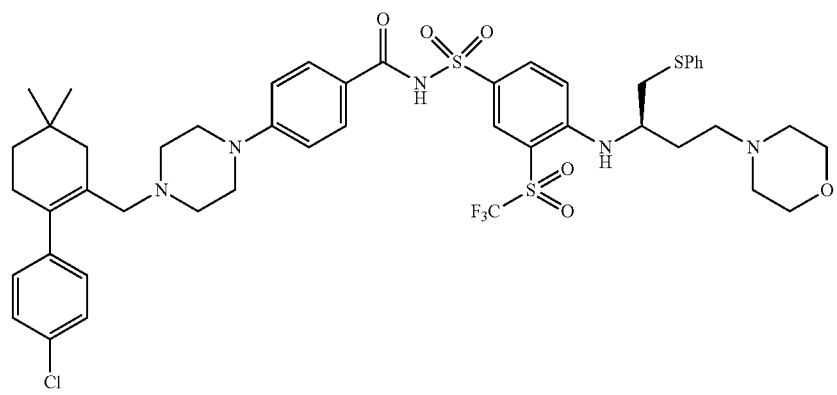

In one aspect, the method may comprise the step of administering to said individual a BCL-2 inhibitor. The BCL-2 inhibitor may be selected from ABT-263 (Navitoclax), ABT-737, ABT-199, GDC-0199, GX15-070 (Obatoclax), and combinations thereof, all available from Abbott Laboratories. In one aspect, the BCL-2 inhibitor may be ABT-263 Suitable BCL-2 inhibitors are described, for example, in US 2017-0087162 A1 to Starczynowski et al, published Mar. 30, 2017.

In one aspect, a method of treating malignant mesothelioma and/or a small cell lung cancer that express midkine is disclosed. The method may comprise the step of administering to an individual in need thereof an effective amount of a pharmaceutical composition comprising a compound selected from

2

3-(2-(4-chlorobenzyl)imidazo[2,1-b]thiazol-6-yl)-2H-chromen-2-one,

3

3-(2-(4-fluorobenzyl)imidazo[2,1-b]thiazol-6-yl)-2H-chromen-2-one,

5

N-(4-fluorophenyl)-6-(4-(methoxymethyl)phenethyl)-2-methyl-5-oxo-5,6-dihydro-1,6-naphthyridine-3-carboxamide,

7

N-(4-chlorobenzyl)-2-methyl-5-oxo-6-(pyridin-3-ylmethyl)-5,6-dihydro-1,6-naphthyridine-3-carboxamide,

8 pharmaceutically acceptable salts thereof, and combinations thereof, and a pharmaceutical carrier.

In one aspect, the above compounds may be administered with a therapeutically effective amount of a BCL-2 inhibitor, for example, ABT-263, or any of the aforementioned BCL-2 inhibitors.

Pharmaceutical Compositions

In one aspect, a composition comprising any one or more compounds or pharmaceutically acceptable salts thereof as disclosed above, in combination with a BCL-2 inhibitor and a pharmaceutically acceptable excipient is disclosed. In one aspect, the BCL-2 inhibitor may be ABT-263. The combination may take any form as disclosed herein.

In one aspect, small molecules provided herein may be administered in an intravenous or subcutaneous unit dosage form; however, other routes of administration are also contemplated. Contemplated routes of administration include but are not limited to oral, parenteral, intravenous, and subcutaneous. In some embodiments, small molecules provided herein can be formulated into liquid preparations for, e.g., oral administration. Suitable forms include suspensions, syrups, elixirs, and the like. In some embodiments, unit dosage forms for oral administration include tablets and capsules. Unit dosage forms configured for administration once a day; however, in certain embodiments it can be desirable to configure the unit dosage form for administration twice a day, or more.

In one aspect, pharmaceutical compositions are isotonic with the blood or other body fluid of the recipient. The isotonicity of the compositions can be attained using sodium tartrate, propylene glycol or other inorganic or organic solutes. An example includes sodium chloride. Buffering agents can be employed, such as acetic acid and salts, citric acid and salts, boric acid and salts, and phosphoric acid and salts. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Viscosity of the pharmaceutical compositions can be maintained at the selected level using a pharmaceutically acceptable thickening agent. Methylcellulose is useful because it is readily and economically available and is easy to work with. Other suitable thickening agents include, for example, xanthan gum, carboxymethyl cellulose, hydroxypropyl cellulose, carbomer, and the like. In some embodiments, the concentration of the thickener will depend upon the thickening agent selected. An amount can be used that will achieve the selected viscosity. Viscous compositions are normally prepared from solutions by the addition of such thickening agents.

A pharmaceutically acceptable preservative can be employed to increase the shelf life of the pharmaceutical compositions. Benzyl alcohol can be suitable, although a variety of preservatives including, for example, parabens, thimerosal, chlorobutanol, or benzalkonium chloride can also be employed. A suitable concentration of the preservative is typically from about 0.02% to about 2% based on the total weight of the composition, although larger or smaller amounts can be desirable depending upon the agent selected. Reducing agents, as described above, can be advantageously used to maintain good shelf life of the formulation.

In one aspect, small molecules provided herein can be in admixture with a suitable carrier, diluent, or excipient such as sterile water, physiological saline, glucose, or the like, and can contain auxiliary substances such as wetting or emulsifying agents, pH buffering agents, gelling or viscosity enhancing additives, preservatives, flavoring agents, colors, and the like, depending upon the route of administration and the preparation desired. See, e.g., "Remington: The Science and Practice of Pharmacy", Lippincott Williams & Wilkins; 20th edition (December 2000) and "Remington's Pharmaceutical Sciences," Mack Pub. Co.; $18^{th}$ and $19^{th}$ editions (1990 and 1995, respectively). Such preparations can include complexing agents, metal ions, polymeric compounds such as polyacetic acid, polyglycolic acid, hydrogels, dextran, and the like, liposomes, microemulsions, micelles, unilamellar or multilamellar vesicles, erythrocyte ghosts or spheroblasts. Suitable lipids for liposomal formulation include, without limitation, monoglycerides, diglycerides, sulfatides, lysolecithin, phospholipids, saponin, bile acids, and the like. The presence of such additional components can influence the physical state, solubility, stability, rate of in vivo release, and rate of in vivo clearance, and are thus chosen according to the intended application, such that the characteristics of the carrier are tailored to the selected route of administration.

For oral administration, the pharmaceutical compositions can be provided as a tablet, aqueous or oil suspension, dispersible powder or granule, emulsion, hard or soft capsule, syrup or elixir. Compositions intended for oral use can be prepared according to any method known in the art for the manufacture of pharmaceutical compositions and can include one or more of the following agents: sweeteners, flavoring agents, coloring agents and preservatives. Aqueous suspensions can contain the active ingredient in admixture with excipients suitable for the manufacture of aqueous suspensions.

Formulations for oral use can also be provided as hard gelatin capsules, wherein the active ingredient(s) are mixed with an inert solid diluent, such as calcium carbonate, calcium phosphate, or kaolin, or as soft gelatin capsules. In soft capsules, the inhibitors can be dissolved or suspended in suitable liquids, such as water or an oil medium, such as peanut oil, olive oil, fatty oils, liquid paraffin, or liquid polyethylene glycols. Stabilizers and microspheres formulated for oral administration can also be used. Capsules can include push-fit capsules made of gelatin, as well as soft, sealed capsules made of gelatin and a plasticizer, such as glycerol or sorbitol. The push-fit capsules can contain the active ingredient in admixture with fillers such as lactose, binders such as starches, and/or lubricants such as talc or magnesium stearate and, optionally, stabilizers.

Tablets can be uncoated or coated by known methods to delay disintegration and absorption in the gastrointestinal tract and thereby provide a sustained action over a longer period of time. For example, a time delay material such as glyceryl monostearate can be used. When administered in solid form, such as tablet form, the solid form typically comprises from about 0.001 wt. % or less to about 50 wt. % or more of active ingredient(s), for example, from about 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, or 1 wt. % to about 2, 3, 4, 5, 6, 7, 8, 9, 10, 15, 20, 25, 30, 35, 40, or 45 wt. %.

Tablets can contain the active ingredients in admixture with non-toxic pharmaceutically acceptable excipients including inert materials. For example, a tablet can be prepared by compression or molding, optionally, with one or more additional ingredients. Compressed tablets can be prepared by compressing in a suitable machine the active ingredients in a free-flowing form such as powder or granules, optionally mixed with a binder, lubricant, inert diluent, surface active or dispersing agent. Molded tablets can be made by molding, in a suitable machine, a mixture of the powdered inhibitor moistened with an inert liquid diluent.

In some embodiments, each tablet or capsule contains from about 1 mg or less to about 1,000 mg or more of a small molecule provided herein, for example, from about 10, 20, 30, 40, 50, 60, 70, 80, 90, or 100 mg to about 150, 200, 250, 300, 350, 400, 450, 500, 550, 600, 650, 700, 750, 800, or 900 mg. In some embodiments, tablets or capsules are provided in a range of dosages to permit divided dosages to be administered. A dosage appropriate to the patient and the number of doses to be administered daily can thus be conveniently selected. In certain embodiments two or more of the therapeutic agents can be incorporated to be administered into a single tablet or other dosage form (e.g., in a combination therapy); however, in other embodiments the therapeutic agents can be provided in separate dosage forms.

Suitable inert materials include diluents, such as carbohydrates, mannitol, lactose, anhydrous lactose, cellulose, sucrose, modified dextrans, starch, and the like, or inorganic salts such as calcium triphosphate, calcium phosphate, sodium phosphate, calcium carbonate, sodium carbonate, magnesium carbonate, and sodium chloride. Disintegrants or granulating agents can be included in the formulation, for example, starches such as corn starch, alginic acid, sodium starch glycolate, Amberlite, sodium carboxymethylcellulose, ultramylopectin, sodium alginate, gelatin, orange peel, acid carboxymethyl cellulose, natural sponge and bentonite, insoluble cationic exchange resins, powdered gums such as agar, karaya or tragacanth, or alginic acid or salts thereof.

Binders can be used to form a hard tablet. Binders include materials from natural products such as acacia, tragacanth, starch and gelatin, methyl cellulose, ethyl cellulose, carboxymethyl cellulose, polyvinyl pyrrolidone, hydroxypropylmethyl cellulose, and the like.

Lubricants, such as stearic acid or magnesium or calcium salts thereof, polytetrafluoroethylene, liquid paraffin, vegetable oils and waxes, sodium lauryl sulfate, magnesium lauryl sulfate, polyethylene glycol, starch, talc, pyrogenic silica, hydrated silicoaluminate, and the like, can be included in tablet formulations.

Surfactants can also be employed, for example, anionic detergents such as sodium lauryl sulfate, dioctyl sodium sulfosuccinate and dioctyl sodium sulfonate, cationic such as benzalkonium chloride or benzethonium chloride, or nonionic detergents such as polyoxyethylene hydrogenated castor oil, glycerol monostearate, polysorbates, sucrose fatty acid ester, methyl cellulose, or carboxymethyl cellulose.

Controlled release formulations can be employed wherein the amifostine or analog(s) thereof is incorporated into an inert matrix that permits release by either diffusion or leaching mechanisms. Slowly degenerating matrices can also be incorporated into the formulation. Other delivery systems can include timed release, delayed release, or sustained release delivery systems.

Coatings can be used, for example, nonenteric materials such as methyl cellulose, ethyl cellulose, hydroxyethyl cellulose, methylhydroxy-ethyl cellulose, hydroxypropyl cellulose, hydroxypropyl-methyl cellulose, sodium carboxymethyl cellulose, providone and the polyethylene glycols, or enteric materials such as phthalic acid esters. Dyestuffs or pigments can be added for identification or to characterize different combinations of inhibitor doses.

When administered orally in liquid form, a liquid carrier such as water, petroleum, oils of animal or plant origin such as peanut oil, mineral oil, soybean oil, or sesame oil, or synthetic oils can be added to the active ingredient(s). Physiological saline solution, dextrose, or other saccharide solution, or glycols such as ethylene glycol, propylene glycol, or polyethylene glycol are also suitable liquid carriers. The pharmaceutical compositions can also be in the form of oil-in-water emulsions. The oily phase can be a vegetable oil, such as olive or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Pulmonary delivery may also be employed. The inhibitor is delivered to the lungs while inhaling and traverses across the lung epithelial lining to the blood stream. A wide range of mechanical devices designed for pulmonary delivery of therapeutic products can be employed, including but not limited to nebulizers, metered dose inhalers, and powder inhalers, all of which are familiar to those skilled in the art. These devices employ formulations suitable for the dispensing of inhibitor. Typically, each formulation is specific to the type of device employed and can involve the use of an appropriate propellant material, in addition to diluents, adjuvants, and/or carriers useful in therapy.

The active ingredients may be prepared for pulmonary delivery in particulate form with an average particle size of from 0.1 µm or less to 10 µm or more, for example, from about 0.2, 0.3, 0.4, 0.5, 0.6, 0.7, 0.8, or 0.9 µm to about 1.0, 1.5, 2.0, 2.5, 3.0, 3.5, 4.0, 4.5, 5.0, 5.5, 6.0, 6.5, 7.0, 7.5, 8.0, 8.5, 9.0, or 9.5 µm. Pharmaceutically acceptable carriers for pulmonary delivery of inhibitor include carbohydrates such as trehalose, mannitol, xylitol, sucrose, lactose, and sorbitol. Other ingredients for use in formulations can include DPPC, DOPE, DSPC, and DOPC. Natural or synthetic surfactants can be used, including polyethylene glycol and dextrans, such as cyclodextran. Bile salts and other related enhancers, as well as cellulose and cellulose derivatives, and amino acids can also be used. Liposomes, microcapsules, microspheres, inclusion complexes, and other types of carriers can also be employed.

Pharmaceutical formulations suitable for use with a nebulizer, either jet or ultrasonic, typically comprise the inhibitor dissolved or suspended in water at a concentration of about 0.01 or less to 100 mg or more of inhibitor per mL of solution, for example, from about 0.1, 1, 2, 3, 4, 5, 6, 7, 8, 9, or 10 mg to about 15, 20, 25, 30, 35, 40, 45, 50, 55, 60, 65, 70, 75, 80, 85, or 90 mg per mL of solution. The formulation can also include a buffer and a simple sugar (e.g., for protein stabilization and regulation of osmotic pressure). The nebulizer formulation can also contain a surfactant, to reduce or prevent surface induced aggregation of the inhibitor caused by atomization of the solution in forming the aerosol.

Formulations for use with a metered-dose inhaler device generally comprise a finely divided powder containing the active ingredients suspended in a propellant with the aid of a surfactant. The propellant can include conventional propellants, such as chlorofluorocarbons, hydrochlorofluorocarbons, hydrofluorocarbons, and hydrocarbons. Example propellants include trichlorofluoromethane, dichlorodifluoromethane, dichlorotetrafluoroethanol, 1,1,1,2-tetrafluoroethane, and combinations thereof. Suitable surfactants include sorbitan trioleate, soya lecithin, and oleic acid.

Formulations for dispensing from a powder inhaler device typically comprise a finely divided dry powder containing inhibitor, optionally including a bulking agent, such as lactose, sorbitol, sucrose, mannitol, trehalose, or xylitol in an amount that facilitates dispersal of the powder from the device, typically from about 1 wt. % or less to 99 wt. % or more of the formulation, for example, from about 5, 10, 15, 20, 25, 30, 35, 40, 45, or 50 wt. % to about 55, 60, 65, 70, 75, 80, 85, or 90 wt. % of the formulation.

In some embodiments, a small molecule provided herein can be administered by intravenous, parenteral, or other injection, in the form of a pyrogen-free, parenterally acceptable aqueous solution or oleaginous suspension. Suspensions can be formulated according to methods well known in the art using suitable dispersing or wetting agents and suspending agents. The preparation of acceptable aqueous solutions with suitable pH, isotonicity, stability, and the like, is within the skill in the art. In some embodiments, a pharmaceutical composition for injection can include an isotonic vehicle such as 1,3-butanediol, water, isotonic sodium chloride solution, Ringer's solution, dextrose solution, dextrose and sodium chloride solution, lactated Ringer's solution, or other vehicles as are known in the art. In addition, sterile fixed oils can be employed conventionally as a solvent or suspending medium. For this purpose, any bland fixed oil can be employed including synthetic mono or diglycerides. In addition, fatty acids such as oleic acid can likewise be used in the formation of injectable preparations. The pharmaceutical compositions can also contain stabilizers, preservatives, buffers, antioxidants, or other additives known to those of skill in the art.

The duration of the injection can be adjusted depending upon various factors, and can comprise a single injection administered over the course of a few seconds or less, to 0.5, 0.1, 0.25, 0.5, 0.75, 1, 2, 3, 4, 5, 6, 7, 8, 9, 10, 11, 12, 13, 14, 15, 16, 17, 18, 19, 20, 21, 22, 23, or 24 hours or more of continuous intravenous administration.

In some embodiments, small molecules provided herein can additionally employ adjunct components conventionally found in pharmaceutical compositions in their art-established fashion and at their art-established levels. Thus, for example, the compositions can contain additional compatible pharmaceutically active materials for combination therapy (such as supplementary antimicrobials, antipruritics, astringents, local anesthetics, anti-inflammatory agents, reducing agents, chemotherapeutics and the like), or can contain materials useful in physically formulating various dosage forms, such as excipients, dyes, thickening agents, stabilizers, preservatives or antioxidants. Anti-cancer agents that can be used in combination with the small molecules provided herein include vinca alkaloids such as vinblastine and vincristine; anthracyclines such as doxorubicin, daunorubicin, epirubicin; anthracenes such as bisantrene and mitoxantrone; epipodophyllo-toxins such as etoposide and teniposide; and other anticancer drugs such as actinomyocin D, mithomycin C, mitramycin, methotrexate, docetaxel, etoposide (VP-16), paclitaxel, docetaxel, and adriamycin); and immunosuppressants (e.g., cyclosporine A, tacrolimus).

In some embodiments, the small molecules provided herein can be provided to an administering physician or other health care professional in the form of a kit. The kit is a package which houses a container which contains the inhibitor(s) in a suitable pharmaceutical composition, and instructions for administering the pharmaceutical composition to a subject. The kit can optionally also contain one or more additional therapeutic agents, e.g., chemotherapeutics currently employed for treating the sarcomas described herein. For example, a kit containing one or more compositions comprising small molecules provided herein in combination with one or more additional chemotherapeutic agents can be provided, or separate pharmaceutical compositions containing a small molecule provided herein and additional therapeutic agents can be provided. The kit can also contain separate doses of a small molecule provided herein for serial or sequential administration. The kit can optionally contain one or more diagnostic tools and instructions for use. The kit can contain suitable delivery devices, e.g., syringes, and the like, along with instructions for administering the inhibitor(s) and any other therapeutic agent. The kit can optionally contain instructions for storage, reconstitution (if applicable), and administration of any or all therapeutic agents included. The kits can include a plurality of containers reflecting the number of administrations to be given to a subject.

Examples

Midkine (MDK) is a heparin-binding growth factor that is highly expressed in many malignant tumors, including lung cancers. We have previously reported that a MDK inhibitor, iMDK, suppresses non-small cell lung cancer expressing MDK without harming normal cells. Importantly, iMDK inhibits the PI3 kinase/Akt pathway and induces apoptosis in MDK expressing non-small cell lung cancer cells. In the present study, Applicant investigated the anti-tumor effect of iMDK against malignant mesothelioma both in vitro and in vivo. 48 hours after treatment, iMDK dose-dependently inhibited cell growth of MDK expressing malignant mesothelioma cells. iMDK also suppressed colony formation of MSTO-211H mesothelioma cells. TUNEL positive cells were significantly increased in MSTO-211H cells 48 hours after iMDK treatment in a dose dependent manner, confirming the induction of apoptosis in mesothelioma cells by iMDK is more effective than each drug alone in MSTO-211H mesothelioma cells. Moreover, systemic administration of iMDK significantly inhibited tumor growth in a mesothelioma xenograft tumor in vivo. Inhibition of MDK with iMDK provides a potential therapeutic approach for the treatment of malignant mesothelioma that is driven by MDK.

3-[2-(4-fluorobenzyl)imidazo [2,1-b][1,3]thiazol-6-yl]-2H-chromen-2-one (herein after "iMDK" (Compound A, below) was purchased from ChemDiv (San Diego, Calif.). Bcl-2 inhibitor: ABT-263 (Compound B) was purchased from Selleck Chemicals (Houston, Tex.).

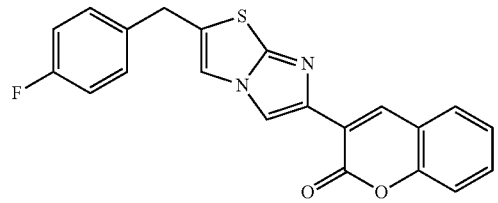

Compound A

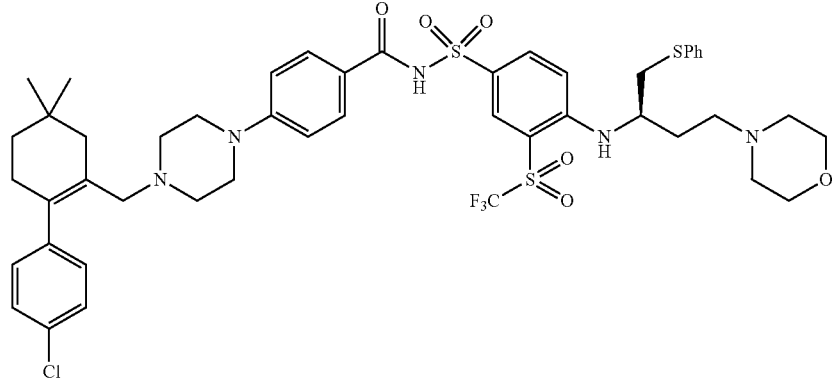

Compound B

Cell lines: The human malignant pulmonary mesothelioma cells MSTO-211H, H2452, H2052, H28 MESO-1 and MESO-4 were grown in RPMI 1640 supplemented with 10% heat-inactivated fetal bovine serum. The human pulmonary adenocarcinoma cells: H441 and the human embryonic kidney cells: HEK293 were grown in high glucose Dulbecco's modified Eagle supplemented with 10% heat-inactivated fetal bovine serum. All cell lines were cultured in 5% CO2 at 37° C.

Antibodies: Antibody specific for β-actin antibody was obtained from Sigma (St. Louis, Mo.) and antibody specific for AKT, phosphorylated-AKT (Ser473), ERK, and phosphorylated-ERK (Ser473) were obtained from Cell Signaling Technology (Beverly, Mass.).

iMDK (Compound A, above) inhibited the cell growth of MDK-positive malignant pulmonary mesothelioma cells both in vitro and in vivo. BCl-2 inhibitor ABT263 enhanced iMDK-mediated suppression of cell proliferation in MSTO-211H mesothelioma cells. Inhibition of MDK with iMDK provides a potential therapeutic approach for the treatment of lung cancers that are driven by MDK.

TABLE

Compounds referenced in the Figures are as follows.

| Compound | Compound structure | Concentration to inhibit midkine protein expression |
|---|---|---|
| 1 ("F6") | 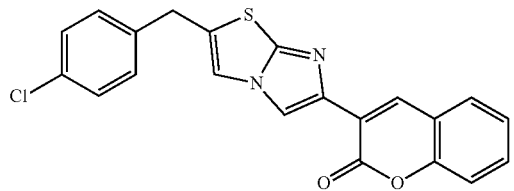 [SMILES: O=c1oc2ccccc2cc1-c1cn2cc(Cc3ccc(Cl)cc3)sc2n1] | 1 uM |
| 2 (iMDK) | 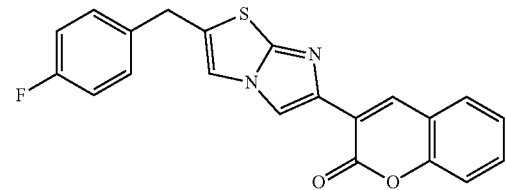 [SMILES: O=c1oc2ccccc2cc1-c1cn2cc(Cc3ccc(F)cc3)sc2n1] | 100 nM |
| 5 ("A6") | 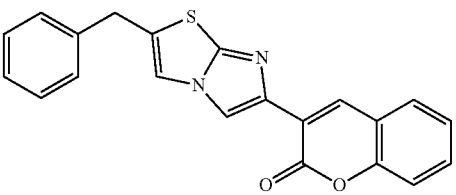 [SMILES: O=c1oc2ccccc2cc1-c1cn2cc(Cc3ccccc3)sc2n1] | 10 μM |
| 6 ("F5") | 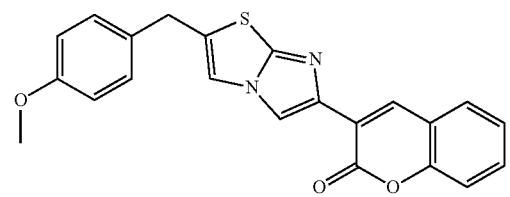 [SMILES: COc1ccc(Cc2cn3cc(-c4cc5ccccc5oc4=O)nc3s2)cc1] | 1 μM |
| 7 | 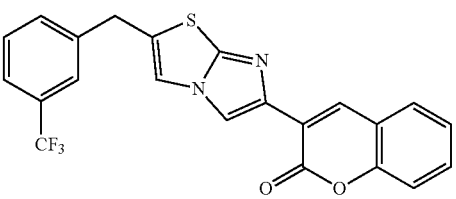 [SMILES: O=c1oc2ccccc2cc1-c1cn2cc(Cc3cccc(C(F)(F)F)c3)sc2n1] | 100 nM |
| 8 ("E6") | 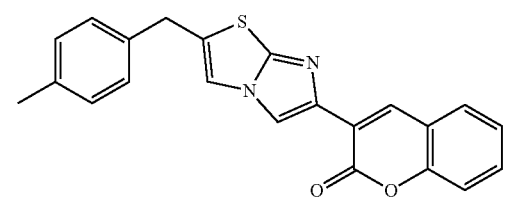 [SMILES: Cc1ccc(Cc2cn3cc(-c4cc5ccccc5oc4=O)nc3s2)cc1] | 1 μM |

TABLE-continued

Compounds referenced in the Figures are as follows.

| Compound | Compound structure | Concentration to inhibit midkine protein expression |
|---|---|---|
| 9 ("D9") | 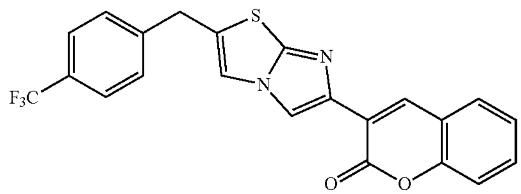 [SMILES: O=c1oc2ccccc2cc1-c1cn2cc(Cc3ccc(C(F)(F)F)cc3)sc2n1] | 1 µM |
| 10 ("F7") | 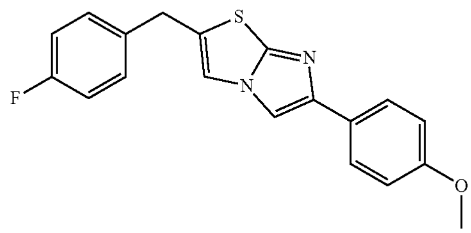 [SMILES: COc1ccc(-c2cn3cc(Cc4ccc(F)cc4)sc3n2)cc1] | 10 µM |

The term "comprising" as used herein is synonymous with "including," "containing," or "characterized by," and is inclusive or open-ended and does not exclude additional, unrecited elements or method steps.

All numbers expressing quantities of ingredients, reaction conditions, and so forth used in the specification are to be understood as being modified in all instances by the term "about." Accordingly, unless indicated to the contrary, the numerical parameters set forth herein are approximations that may vary depending upon the desired properties sought to be obtained. At the very least, and not as an attempt to limit the application of the doctrine of equivalents to the scope of any claims in any application claiming priority to the present application, each numerical parameter should be construed in light of the number of significant digits and ordinary rounding approaches.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention.

All percentages and ratios are calculated based on the total composition unless otherwise indicated.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "20 mm" is intended to mean "about 20 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

What is claimed is:

1. A method of treating malignant mesothelioma comprising administering to an individual in need thereof an effective amount of a pharmaceutical composition comprising the compound

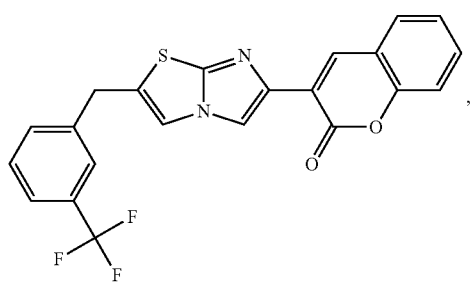 [SMILES: O=c1oc2ccccc2cc1-c1cn2cc(Cc3cccc(C(F)(F)F)c3)sc2n1]

or a pharmaceutically acceptable salt thereof, and a pharmaceutical carrier.

2. The method of claim 1, further comprising administering to said individual a therapeutically effective amount of a BCL-2 inhibitor, wherein said administration of BCL-2 inhibitor is administered serially with the compound of claim 1, in combination with the compound of claim 1, simultaneously with the compound of claim 1, or combinations thereof.

3. The method of claim 2, wherein said BCL-2 inhibitor is selected from ABT-737, ABT-199, GDC-0199, GX15-070 (Obatoclax), and combinations thereof.

4. The method of claim 1, further comprising administering to said individual a therapeutically effective amount of

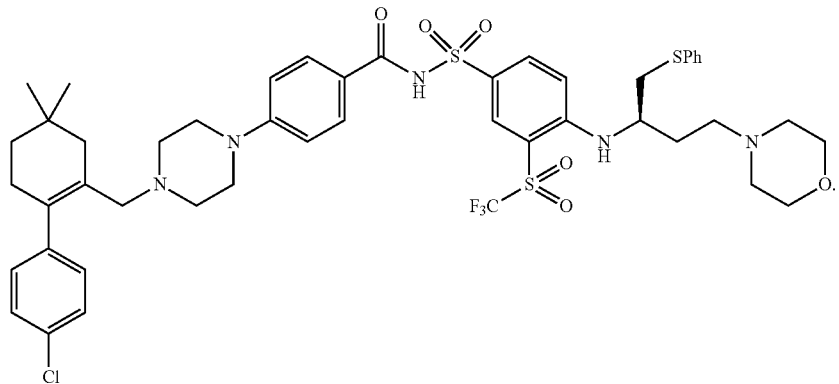

("ABT-263")

5. The method of claim 1, wherein ABT-263 is administered in combination with the compound of claim 1.

6. The method of claim 1, wherein ABT-263 is administered serially with the compound of claim 1.

7. The method of claim 1, wherein ABT-263 is administered simultaneously with the compound of claim 1.

8. The method of claim 1, wherein said individual is a mammal.

9. The method of claim 1, wherein said individual is human.

* * * * *